US006933302B2

(12) United States Patent
Yang

(10) Patent No.: US 6,933,302 B2
(45) Date of Patent: Aug. 23, 2005

(54) NITROGEN-BASED HOMO-CAMPTOTHECIN DERIVATIVES

(75) Inventor: Li-Xi Yang, San Francisco, CA (US)

(73) Assignees: California Pacific Medical Center, San Francisco, CA (US); Catholic Healthcare West, San Francisco, CA (US)

( * ) Notice: Subject to any disclaimer, the term of this patent is extended or adjusted under 35 U.S.C. 154(b) by 0 days.

(21) Appl. No.: 10/454,718

(22) Filed: Jun. 3, 2003

(65) Prior Publication Data

US 2004/0063740 A1 Apr. 1, 2004

Related U.S. Application Data

(60) Provisional application No. 60/385,468, filed on Jun. 3, 2002.

(51) Int. Cl.[7] ................... A61K 31/437; C07D 471/14; C07D 413/06
(52) U.S. Cl. .......................... 514/283; 546/48; 546/50; 544/111; 544/125
(58) Field of Search ..................... 546/48, 50; 514/283; 544/111, 125

(56) References Cited

U.S. PATENT DOCUMENTS

| | | | |
|---|---|---|---|
| 4,399,282 A | 8/1983 | Miyasaka |
| 4,943,579 A | 7/1990 | Vishnuvajjala et al. |
| 5,916,896 A | 6/1999 | Wall et al. |
| 5,965,566 A | 10/1999 | Greenwald et al. |
| 6,028,078 A | 2/2000 | Hausheer et al. |
| 6,040,313 A | 3/2000 | Wall et al. |
| 6,057,303 A | 5/2000 | Haridas et al. |
| 6,096,336 A | 8/2000 | Cao et al. |
| 6,113,906 A | 9/2000 | Greenwald et al. |
| 6,114,529 A | 9/2000 | Kawaguchi et al. |
| 6,120,793 A | 9/2000 | Cao et al. |
| 6,127,355 A | 10/2000 | Greenwald et al. |
| 6,153,655 A | 11/2000 | Martinez et al. |
| 6,207,832 B1 | 3/2001 | Curran et al. |
| 6,339,091 B1 * | 1/2002 | Bigg et al. .................. 514/283 |
| 6,350,756 B1 | 2/2002 | Yang et al. |
| 6,403,604 B1 | 6/2002 | Yang et al. |

FOREIGN PATENT DOCUMENTS

| | | |
|---|---|---|
| EP | 0 861 842 A | 9/1998 |
| JP | 2524804 * | 8/1996 |
| WO | WO 95/10304 A1 | 4/1995 |
| WO | WO 96/26950 A1 | 9/1996 |
| WO | WO 97/19085 A1 | 5/1997 |
| WO | WO 97/28165 | 8/1997 |
| WO | WO 98/13059 A1 | 4/1998 |
| WO | WO 98/14459 A1 | 4/1998 |
| WO | WO 98/28304 A1 | 7/1998 |
| WO | WO 98/35940 | 8/1998 |
| WO | WO 98/51703 A1 | 11/1998 |
| WO | WO 99/17805 A1 | 4/1999 |
| WO | WO 00/66127 A1 | 11/2000 |
| WO | WO 00/67801 A2 | 11/2000 |
| WO | WO 03/014069 A1 | 2/2003 |

OTHER PUBLICATIONS

English Abstract DN 112:158710 Nagao Yoshimitsu et al Aug. 1996.*
Franciscus M et al , May 2002 Novel 20–carbononate Linked prodrugs of Camptothecin . . . pp. 2371–2376.*
Olivier Lavergne et al Jul. 1998,Homocamptothecins . . . , 5410–5419.*
Oliveir Lavergne et al et al Mar. 2000 , Topoisomerase I–mediated . . . pp. 2285–2289.*
Laurence Lesueur –Ginot et al Jun. 1999, Homocamptothecin , an E–ring Modified . . . .*
Bom et al., "The Novel Silatecan 7–tert–Butyldimethylsilyl–10–hydroxycamptothecin Displays High Lipophilicity, Improved Human Blood Stability, and Potent Anticancer Activity", *J. Med. Chem.*, 2000, 43, 3940–3980.
Bomgaars, et al., "The Development of Camptothecin Analogs in Childhood Cancers," Oncologist 6:506–516 (2001).
Cao et al., "Alkyl Esters of Camptothecin and 9–Nitrocamptothecin: Synthesis, in Vitro Pharmacokinetics, Toxicity, and Antitumor Activity", *J. Med. Chem*, 1998, 41, 31–37.
Dallavalle et al. "Novel 7–Substituted Camptothecins with Potent Antitumor Activity", *J. Med. Chem*, 2000, 43, 3963–3969.
Del poeta et al., "Comparison of In Vitro Activities of Camtothecin and Nitidine Derivatives Against Fungal and Cancer Cells", *Antimicrobial Agents and Chemotherapy*, Dec. 1999, 2862–2868.
Garcia–Carbonero et al., "Current Perspectives on the Clinical Experience, Pharmacology and Continued Development of the Camptothecins", *Clinical Cancer Research*, Mar. 2002, vol. 8, 641–661.
Keskin, et al., "Characterization of anticancer agents by their growth inhibitory activity and relationships to mechanism of action and structure", Anti Cancer Drug Design, 15:2:78–98 (2000).
Kingsbury et al., "Synthesis of Water–Soluble (Aminoalkyl)camptothecin Analogues: Inhibition of Topoisomerase I and Antitumor Activity", *J. Med. Chem*, 1991, 34, 98–107.
Lavergne et al., *Ann. N.Y. Acad. Sci.* 2000, 922:100–111.
Lerchen, "Milestones in Camptothecin Research," Drugs of the Future 27:869–876 (2002).

(Continued)

*Primary Examiner*—Rita Desai
(74) *Attorney, Agent, or Firm*—Foley & Lardner LLP; Tom M. Moran

(57) ABSTRACT

(20) esters of camptothecin analogs are provided. The compounds are (20) esters of an aminoalkanoic acid or an imidoalkanoic acid and homocamptothecin, which is optionally substituted at the 7, 9, 10, 11, and 12 positions of the homocamptothecin ring. The compounds are useful for treating cancer.

50 Claims, No Drawings

OTHER PUBLICATIONS

Maliepaard et al., "Circumvention of breast cancer resistance protein (BCRP)–mediated resistance to camptothecins in vitro using non–substrate drugs or the BCRP inhibitor GF120918," *Clinical Cancer Research* 7:935–941, 2001.

Nomoto et al., "Characterization of a human small–cell lung cancer cell line resistant to a new water–soluble camptothecin derivative, DX–8951f," *Jpn. J. Cancer Res.* 89:1179–1186, 1998.

O'Leary et al., "Camptothecins: a Review of their Development and Schedules of Administration", *European Journal of Cancer*, 1998, vol. 54, No. 10, 1500–1508.

Perego et al., "A Novel 7–modified Camptothecin Analog Overcomes Breast Cancer Resistance Protein–associated Resistance in a Mitoxantrone–selected Colon Carcinoma Cell Line", *Cancer Research*, Aug. 15, 2001, 61, 6034–6037.

Pollack et al., "Potent topoisomerase I inhibition by novel silatecans eliminates glioma proliferation in vitro and in vivo," Cancer Research 59:4898–4905, 1999.

Saltz L. et al., "CPT–11 (Irinotecan) and 5–Fluorouracil: a Promising Combination for Therapy of Colorectal Cancer", European Journal of Cancer, 1996, vol. 32A, No. Suppl. 3, pp. 524–531.

Sawada et al., "Chemical Modification of an Antitumor Alkaloid Camptothecin: Synthesis and Antitumor Activity of 7–C–Substituted Camptothecins", *Chem. Pharm. Bull.*, 1991, 39(10), 2574–2580.

Sawada et al., "Synthesis and Antitumor Activity of 20(S)–Camptothecin Derivatives: Carbamate–Linked, Water–Soluble Derivatives of 7–Ethyl–10–hydroxycamptothecin", *Chem. Pharm. Bull.*, 1991, 39(6) 1446–1454.

Shabat D et al., "Multiple event activation of a generic prodrug trigger by antibody catalysis", Proceedings of the National Academy of Sciences of USA, 96:6925–6930, Jun. 1999.

Singer et al., "Conjugation of Camptothecins to Poly–(L–Glutamic Acid)", Annals of the New York Academy of Sciences, 2000, vol. 922, pp. 136–150.

Takayama et al., "Synthesis of a New Class of Camptothecin Derivatives, The Long–Chain Fatty Acid Esters of 10–Hydroxycamptothecin, as a Potent Prodrug Candidate, and Their In Vitro Metabolic Conversion by Carboxylesterases", *Bioorganic & Medicinal Chemistry Letters*, 1998, 8, 415–518.

Wall et al., "Camptothecin and Taxol: Discovery to Clinic—Thirteenth Bruce F. Cain Memorial Award Lecture", *Cancer Research*, Feb. 15, 1995, 55, 753–760.

Wall et al., "Plant Antitumor Agents, 30.$^{1a,b}$ Synthesis and Structure Activity of Novel Camptothecin Analogs", *J. Med. Chem.*, 1993, 36, 2689–2700.

XP 002033248, ABSTRACT, WPI, vol. 46, N0. 89.

XP 002033250 ABSTRACT, WPI, vol. 45, N0. 89.

Zhao et al., "Synthesis, Topoisomerase I Inhibitory Activity and In Vitro Cytotoxicity of Camptothecin Derivatives Bearing Five–Membered Heterocycle Containing 10–Substituents", *Anti–Cancer Drug Design*, 1998, 13, 145–157.

* cited by examiner

NITROGEN-BASED HOMO-CAMPTOTHECIN DERIVATIVES

CROSS-REFERENCE TO RELATED APPLICATION

This application claims priority under 35 U.S.C. §119(e) to U.S. Provisional Application No. 60/385,468, filed Jun. 3, 2002, the entire content of which is hereby incorporated by reference.

FIELD OF THE INVENTION

This invention relates to novel nitrogen based homo-camptothecin derivatives that are useful for treating various types of cancer.

BACKGROUND OF THE INVENTION

Camptothecin ("CPT"), shown below, is an indole alkaloid natural product isolated from the oriental tree *Camptotheca acuminata*, which has substantial anti-tumor activity in animal models. The compound has a pentacyclic ring system with an asymmetric center in ring E with a 20 S configuration. The pentacyclic ring system includes a pyrrolo [3, 4-b] quinoline (rings A, B and C), a conjugated pyridone ring D), and six membered lactone (ring E) with an 20α-hydroxyl group.

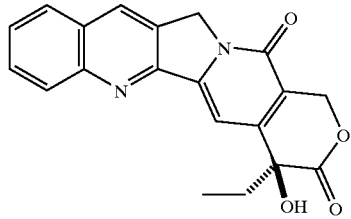

Subsequent studies established that CPT inhibited both DNA and RNA synthesis. Recent research has demonstrated that CPT and CPT analogues interfere with the mechanism of action of the cellular enzyme topoisomerase I, which is important in a number of cellular processes (e.g., DNA replication and recombination, RNA transcription, chromosome decondensation, etc.).

A significant problem with CPT and CPT analogues is the chemical lability of the α-hydroxy lactone functionality. Rapid in situ hydrolysis of the α-hydroxy lactone provides a ring opened carboxylate form which is relatively inactive, as was shown in early clinical studies with CPT sodium.

One solution to the chemical instability of the α-hydroxy lactone group found in CPT is insertion of a carbon atom between the free hydroxy group and the carbonyl carbon of the lactone group to provide a ring expanded β-hydroxy lactone known as homo-Camptothecin ("hCPT"), which is shown below. hCPT is considerably more stable than CPT because of the reduced susceptibility of the lactone carbonyl to nucleophilic attack. Importantly, possesses substantial anti-proliferative activity in animal studies.

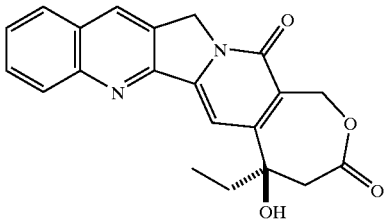

Accordingly there is a need for new analogues of hCPT that may be stable anti-proliferative agents.

SUMMARY OF THE INVENTION

One aspect of this invention is a compound of the formula (I), below,

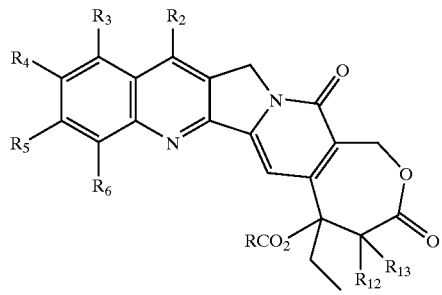

wherein R is $R_aR_bN$—$(CH2)m$;

m is an integer from 1–10; and (i) one of $R_a$ or $R_b$ is H and the other is lower alkyl substituted with one to five substituents independently selected from the group consisting of halo, lower alkoxy, hydroxy, cyano, nitro, or amino;

phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperidino, lower alkoxycarbonyl, and lower alkylcarbonylamino;

cycloalkyl of 3–7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; or lower alkoxy; or (ii) each of $R_a$ and $R_b$ is independently a substituent as above; or (iii) $R_aR_b$ together with N form a cyclic amine or imide ring; and $R_2$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, —C(O)H, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonylmethyl, benzoylmethyl, benzylcarbonyloxymethyl, or mono- or di lower alkoxymethyl;

$R_3$ is hydrogen, halo, lower alkyl, lower alkoxy, hydroxy, RC(O)O (R defined hereinbefore) cyano, nitro, amino, halogenated lower alkyl, halogenated lower alkoxy, hydroxycarbonyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), —C(O)H, $CH_2$ $R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, or lower alkylcarbonylamino;

$R_4$ is hydrogen, halo, lower alkyl, lower alkoxy, hydroxy, RC(O)O (R defined hereinbefore) cyano, nitro, amino, amino lower alkyl, halogenated lower alkyl, halogenated lower alkoxy, hydroxycarbonyl, lower alkoxycarbonyl, carbamoyloxy, lower alkylcarbonyloxy, or lower alkylcarbonylamino, or $R_4$ together with $R_5$ is methylenedioxy or ethylenedioxy;

$R_5$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, lower alkoxycarbonyl, lower alkylcarbonyloxy, or lower alkylcarbonylamino or $R_5$ together with $R_4$ is methylenedioxy or ethylenedioxy;

$R_6$ is hydrogen, halo, lower alkyl, lower alkoxy, hydroxy, RC(O)O (R defined hereinbefore), cyano, nitro, amino, halogenated lower alkyl, halogenated lower alkoxy, hydroxcarbonyl, lower alkoxycarbonyl, lower alkylcarbonyloxy, or lower alkylcarbonylamino; and $R_{12}$ and $R_{13}$ are independently hydrogen, lower alkyl, cyano, hydroxycarbonyl, lower alkoxycarbonyl, cycloalkyl, alkylcarbonylamino, 1-napthyl, 2-napthyl or phenyl.

Another aspect of the invention is a pharmaceutical composition useful for treating cancer in a warm-blooded animal, which composition comprises compound of the invention as defined herein in combination with a pharmaceutically acceptable excipient.

Another aspect of this invention is a method for treating cancer in a warm-blooded animal, which method comprises administering a therapeutically effective amount of a compound of the invention as defined herein. The compound is administered in a therapeutically effective dose by appropriate administration, e.g., orally, topically, or parenterally.

Another aspect of this invention is process for preparing compounds of this invention by reacting camptothecin (hCPT) or a hCPT analog with a compound of the formula R—C(O)X, wherein R is $R_aR_bN(CH_2)_2$, where $R_a$ and $R_b$ are as defined herein, and X is e.g., bromide, chloride, hydroxy, alkoxy of 1–11 carbons.

Other aspects of this invention will be apparent to one of skill in the art by reviewing the ensuing specification.

DETAILED DESCRIPTION

Overview

In general this invention can be viewed as a (C-20) ester of hCPT or a hCPT analogue (preferably, a (20S) ester of hCPT or a hCPT analogue). hCPT has a hydroxy at the 20 position, which may be esterified in accordance with the process of this invention to form the corresponding ester in good yield. The resulting ester is unique in that it has an electronegative entity in the chain, which is believed to aid in stabilizing the E ring of the homo-camptothecin molecule. The novel compounds of the invention are active against tumors in mice and are generally well tolerated. They are useful for treating various types of cancer and can be formulated to prepare pharmaceutical preparations for oral, topical, or parenteral administration.

While not wishing to be bound by any particular mechanism of action or theoretical explanation of how the compounds work, it is believed that the C-20 esters exert their effect in part by stabilizing the E ring of the hCPT molecule. The esters may accomplish this through steric hinderance by preventing enzymatic access to the E ring, through the presence of an electron-withdrawing group in the ester chain, i.e., a nitrogen atom, and through facilitating the hydrogen-binding or Van Der Waals forces of the E ring end of the hCPT molecule with the enzyme to inhibit binding and thus enzyme activity to sever the E ring.

Definitions

The term "hCPT" is an abbreviation for homo-camptothecin, which may be synthesized from CPT by methods known in the art. The chemical formula of homo-camptothecin and its numbering system are as follows:

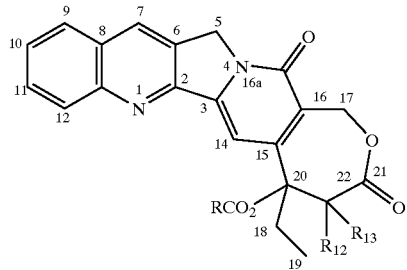

The compound has a hydroxy at the 20-position that may be esterified to make the compounds of this invention. The numbring system for CPT is based on the system for CPT as set forth in U.S. Pat. No. 6,403,604 issued to Yang, et.al Jun. 11, 2002, which patent in its entirety is incorporated herein by reference.

The term "alkyl" refers to a monovalent, saturated aliphatic hydrocarbon radical having the indicated number of carbon atoms. For example, a "C1–6 alkyl" or an "alkyl of 1–6 carbons" or "Alk 1–6" would refer to any alkyl group containing one to six carbons in the structure. "C1–20 alkyl" refers to any alkyl group having one to twenty carbons. Alkyl may be a straight chain (i.e., linear) or a branched chain. Lower alkyl refers to an alkyl of 1–6 carbons. Representative examples lower alkyl radicals include methyl, ethyl, n-propyl, n-butyl, n-pentyl, n-hexyl, isopropyl, isobutyl, isopentyl, amyl, sec-butyl, tert-butyl, tert-pentyl and the like. Higher alkyl refers to alkyls of seven carbons and above. These include n-heptyl, n-octyl, n-nonyl, n-decyl, n-dodecyl, n-tetradecyl, n-hexadecyl, n-octadecyl, n-eicosyl, and the like, along with branched variations thereof. The radical may be optionally substituted with substituents at positions that do not significantly interfere with the preparation of compounds falling within the scope of this invention and that do not significantly reduce the efficacy of the compounds. The alkyl may be optionally substituted with one to five substituents independently selected from the group consisting of halo, lower alkoxy, hydroxy, cyano, nitro, or amino.

The term "alkoxy" refers to a monovalent radical of the formula RO—, where R is an alkyl as defined herein. Lower alkoxy refers to an alkoxy of 1–6 carbon atoms, with higher alkoxy is an alkoxy of seven or more carbon atoms. Representative lower alkoxy radicals include methoxy, ethoxy, n-propoxy, n-butoxy, n-pentyloxy, n-hexyloxy, isopropoxy, isobutoxy, isopentyloxy, amyloxy, sec-butoxy, tert-butoxy, tert-pentyloxy, and the like. Higher alkoxy radicals include those corresponding to the higher alkyl radicals set forth herein. The radical may be optionally substituted with substituents at positions that do not significantly interfere with the preparation of compounds falling within the scope of this invention and that do not significantly reduce the efficacy of the compounds. The radical may be optionally substituted with one to five substituents independently selected from the group consisting of halo, lower alkyl, lower alkoxy, hydroxy, cyano, nitro, or amino.

The term "cycloalkyl" refers to a monovalent, alicyclic, saturated hydrocarbon radical having three or more carbons forming the ring. While known cycloalkyl compounds may have up to 30 or more carbon atoms, generally there will be three to seven carbons in the ring. The latter include, for example, cyclopropyl, cyclobutyl, cyclopentyl, cyclohexyl, and cycloheptyl. The radical may be optionally substituted with substituents at positions that do not significantly interfere with the preparation of compounds falling within the scope of this invention and that do not significantly reduce the efficacy of the compounds. The cycloalkyl is optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

The term "hydroxycarbonyl" is a monovolent radical having the formula —C(O)OH.

The term "lower alkoxycarbonyl" is a monovalent radical having the formula —C(O)OAlk, where Alk is lower alkyl.

The term "lower alkylcarboxyloxy" is a monovalent radical having the formula —OC(O)Alk, where Alk is lower alkyl.

The term "lower alkylcarbonylamino" is a monovalent radical having the formula —NHC(O)Alk, where Alk is lower alkyl.

A "halo" substitutent is a monovalent halogen radical chosen from chloro, bromo, iodo, and fluoro. A "halogenated" compound is one substituted with one or more halo sustituent.

A "phenyl" is a radical formed by removal of a hydrogen from a benzene ring. The phenyl is optionally substituted with from one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino.

A "carbamoyloxy" is a monovalent radical of the formula $R_{13}R_{14}NC(O)O$— (i.e., an aminocarbonyloxy) where $R_{13}$ and $R_{14}$ together form a cyclic amino with the nitrogen atom, or each of $R_{13}$ and $R_{14}$ is independently hydrogen, lower alkyl, hydroxy lower alkyl, hydroxy lower alkyl, amino lower alkyl, lower cycloalkyl, phenyl (substituted or unsubstituted), or benzyl (substituted or unsubstituted). Examples include aminocarbonyloxy, methylaminocarbonyloxy, dimethyl aminocarbonyloxy, [4-(1-piperidino)-1-piperidino] carbonyloxy, 1-morpholinocarbonyloxy, 1-pyrrolidinyl, 1-piperazinecarbonyloxy, and others delineated herein.

A "5-membered heterocyclic ring" is a monovalent radical of a 5-member closed ring containing carbon and at least one other element, generally nitrogen, oxygen, or sulfur and may be fully saturated, partially saturated, or unsaturated (i.e., aromatic in nature). Generally the heterocycle will contain no more than two hetero atoms. Representative examples of unsaturated 5-membered heterocycles with only one hetero atom include 2- or 3-pyrrolyl, 2- or 3-furanyl, and 2- or 3-thiophenyl. Corresponding partially saturated or fully saturated radicals include 3-pyrrolin-2-yl, 2- or 3-pyrrolidinyl, 2- or 3-tetrahydrofuranyl, and 2- or 3-tetrahydrothiophenyl. Representative unsaturated 5-membered heterocyclic radicals having two hetero atoms include imidazolyl, oxazolyl, thiazolyl, pyrazolyl, and the like. The corresponding fully saturated and partially saturated radicals are also included. The heterocyclic radical is bonded through an available carbon atom in the heteocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "6-membered heterocyclic ring" is a monovalent radical of a 6-member closed ring containing carbon and at least one other element, generally nitrogen, oxygen, or sulfur and may be fully saturated, partially saturated, or unsaturated (i.e., aromatic in nature). Generally the heterocycle will contain no more than two hetero atoms. Representative examples of unsaturated 6-membered heterocycles with only one hetero atom include 2-, 3-, or 4-pyridinyl, 2H-pyranyl, and 4H-pryanyl. Corresponding partially saturated or fully saturated radicals include 2-, 3-, or 4-piperidinyl, 2-, 3-, or 4-tetrahydropyranyl and the like. Representative unsaturated 6-membered heterocyclic radicals having two hetero atoms include 3- or 4-pyridazinyl, 2-, 4-, or 5-pyrimidinyl, 2-pyrazinyl, and the like. The corresponding fully saturated and partially saturated radicals are also included, e.g., 2-piperazine. The heterocyclic radical is bonded through an available carbon atom in the heterocyclic ring. The radical may be optionally substituted with substituents at positions that do not significantly interfere with the preparation of compounds falling within the scope of this invention and that do not significantly reduce the efficacy of the compounds. The ring is optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

A "cyclic amino" is a monovalent radical of a saturated 5-, 6-, or 7-membered cyclic amine ring having no more than one additional hetero atom such as nitrogen, oxygen, or sulfur, or a 5-, 6-, or 7-membered cyclic amine fused to another, carbocyclic ring or rings. Representative examples include, e.g., 1-pyrrolidino, 1-piperidino, morpholino, piperazino, 3-benzopiperidino, and the like. These may be substituted or unsubstituted. If substituted, generally they will have no more than 2 substituents chosen from lower alkyl, lower cycloalkyl, hydroxy lower alkyl, phenyl (substituted or unsubstituted), benyzl (substituted or unsubstituted), aminocarbonylmethyl, lower alkylaminocarbonylmethyl, amino, mono- or di-lower alkylamino, cyclic amino, or a 5- or 6-membered heterocyclic ring.

An "imide ring" is a cyclic imide wherein the nitrogen of the cyclic structure is bonded on each side to a carbonyl group, which in turn is bound to carbon atoms to form a ring. An imide ring would include, e.g., phthalimide (which may be substituted on the benzene ring)maleimide, 1,8-naphthalimide (which may be substituted on the naphthyl ring— e.g 3-nitro-1,8-naphthalimide, 4-nitronaphalimide, 4-bromo-napthalimide, and the like). Others will be apparent to one of skill in the art.

Other chemical terms are given their standard meaning as understood by one of skill in the art with guidance from standard texts and dictionaries.

The term "MTD" is the abbreviation for maximum tolerated does.

The term "nM" is the abbreviation for nanomolar.

The term "ip" is the abbreviation for intraperitonial.

Compounds of the Invention

One aspect of this invention is a compound of the formula

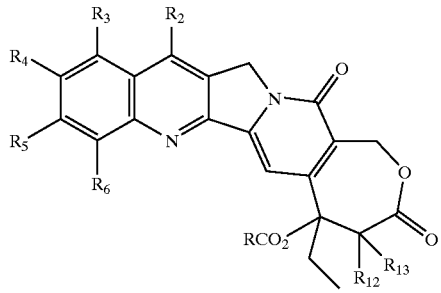

wherein R is $R_aR_bN$—$(CH2)m$; m is an integer from 1–10; and (i) one of $R_a$ or $R_b$ is H and the other is
  lower alkyl substituted with one to five substituents independently selected from the group consisting of halo, lower alkoxy, hydroxy, cyano, nitro, or amino;
  phenyl optionally substituted with from one to five substituents independently selected from the group consisting of halo, lower alkyl, lower alkoxy, hydroxy, cyano, nitro, amino, halogenated lower alkyl, halogenated lower alkoxy, formyl, lower alkyl carbonyl, hydroxycarbonyl, lower alkylcarbonyloxy, benzyloxy, optionally substituted piperidino, lower alkoxycarbonyl, and lower alkylcarbonylamino;
  cycloalkyl of 3–7 carbons, optionally substituted with one to five substituents independently selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino; or
  lower alkoxy; or
(ii) each of $R_a$ and $R_b$ is independently a substituent as above; or
(iii) $R_aR_b$ together with N form a cyclic amine or imide ring; and $R_2$ is hydrogen, halo, lower alkyl, lower alkoxy, hydroxy, RC(O)O (R defined hereinbefore) cyano, nitro, amino, halogenated lower alkyl, halogenated lower alkoxy, hydroxycarbonyl, —C(O)H, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl mono- or di lower alkoxymethyl, alkoxyiminomethyl, methylpiperazinomethyl, or together with $R_3$ is —$CH_2(NH_2)CH_2CH_2$—;

$R_3$ is hydrogen, halo, lower alkyl, lower alkoxy, hydroxy, RC(O)O (R defined hereinbefore) cyano, nitro, amino, halogenated lower alkyl, halogenated lower alkoxy, hydroxycarbonyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), —C(O)H, $CH_2$ $R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, lower alkylcarbonylamino or trialkysilylethylene;

$R_4$ is hydrogen, halo, lower alkyl, lower alkoxy, hydroxy, RC(O)O (R defined hereinbefore) cyano, nitro, amino, amino lower alkyl, halogenated lower alkyl, halogenated lower alkoxy, hydroxycarbonyl, lower alkoxycarbonyl, carbamoyloxy, lower alkylcarbonyloxy, or lower alkylcarbonylamino, or $R_4$ together with $R5_3$ is methylenedioxy or ethylenedioxy;

$R_5$ is hydrogen, halo, lower alkyl, lower alkoxy, hydroxy, RC(O)O (R defined hereinbefore), cyano, nitro, amino, halogenated lower alkyl, halogenated lower alkoxy, hydroxycarbonyl, lower alkoxycarbonyl, lower alkylcarbonyloxy, or lower alkylcarbonylamino or together with $R_4$ is methylenedioxy or ethylenedioxy;

$R_6$ is hydrogen, halo, lower alkyl, lower alkoxy, hydroxy, RC(O)O (R defined hereinbefore), cyano, nitro, amino, halogenated lower alkyl, halogenated lower alkoxy, hydroxcarbonyl, lower alkoxycarbonyl, lower alkylcarbonyloxy, or lower alkylcarbonylamino; and $R_{12}$ and $R_{13}$ are independently hydrogen, lower alkyl, cyano, hydroxycarbonyl, lower alkoxycarbonyl, cycloalkyl, alkylcarbonylamino, 1-napthyl, 2-napthyl or phenyl. Preferred aspects of the compounds of this invention are set forth herein in the specification and claims.

A preferred aspect is a compound of formula (I) wherein each $R_2$, $R_3$, $R_4$, $R_5$, $R_6$, $R_{12}$ and $R_{13}$ is H (or the preferences given hereinafter), m is 2, and $R_aR_bN$ is a cyclic amino or cyclic imido radical.

Another preferred aspect is a compound of formula (I) wherein each $R_2$, $R_3$, $R_4$, $R_5$, $R_6$, $R_{12}$ and $R_{13}$ is H (or the preferences given hereinafter), m is 2, and $R_a$ $R_bNCH_2$—$CH_2$ is one of the following cyclic amino ethyl or cyclic imido ethyl radicals:

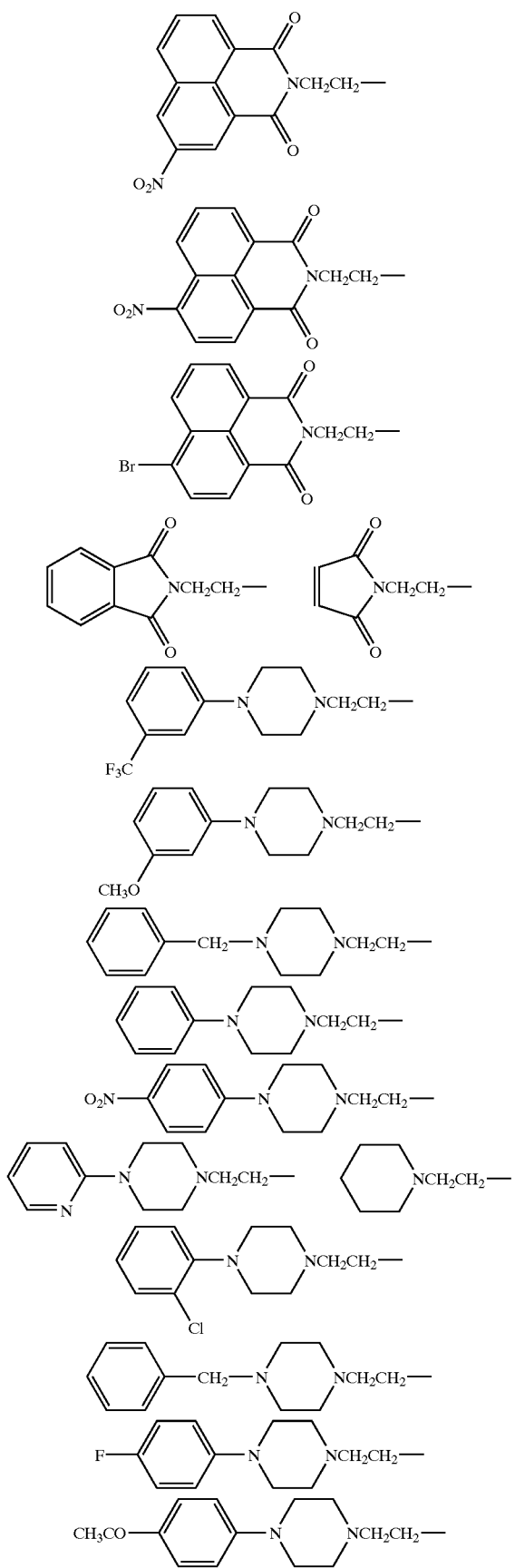
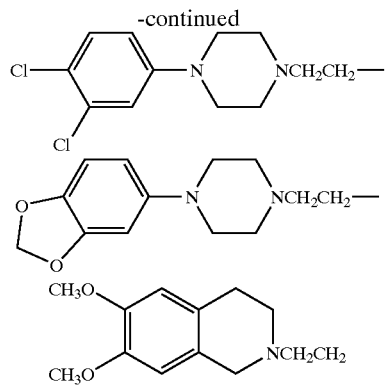

Other aspects of the invention include compounds as described hereinbefore, but where each $R_2$, $R_3$, $R_4$, $R_5$, $R_6$, $R_{12}$ and $R_{13}$ may be a substituent other than only hydrogen. These include, for example, the preferred subgroups set forth hereinafter:

The compound of formula (I), wherein $R_6$ is hydrogen, particularly a compound wherein $R_4$ and $R_5$ together are methylenedioxy and wherein $R_2$ is hydrogen. Of these the compounds particular interest are those where $R_3$ is nitro, amino, methyl, chloro, cyano, acetoxy, or acetylamino.

A compound of formula (I), wherein each of $R_5$ and $R_6$ is hydrogen, especially those wherein $R_3$ is hydrogen; $R_2$ is (3-chloro-n-propyl)dimethylsilyl, tert-butyldimethylsilyl, acetoxymethyl, cyano, formylethenyl, ethoxycarbonyl-ethenyl, cyanoethenyl, 2,2-dicyanoethenyl, (2-cyano-2-ethoxycarbony)ethenyl, ethoxycarbonylethyl, methyl, ethyl, or n-propyl; and $R_4$ is hydroxy, acetoxy, amino, nitro, cyano, chloro, bromo, fluoro, lower alkyl, higher alkyl, lower alkoxy, carbamoyloxy, or formyl. Of these, the compounds wherein $R_2$ is ethyl and $R_4$ is carbamoyloxy are of further interest. Carbamoyloxy substituents that are preferred include 1-pyrazinylcarbonyloxy, 4-(i-propylaminocarbonylmethyl)-1-pyrazinyl-carbonyloxy, or [4-(1-piperidio)-1-piperidinocarbonyloxy.

The compound of formula (I), wherein each of $R_2$, $R_5$, and $R_6$ is hydrogen, for example, those wherein $R_3$ is amino, nitro, cyano, halo, OH, lower alkylamino, di-lower alkylamino, lower alkyl, lower alkoxy, 1-piperidino, 1-mopholino, aminomethyl, lower alkylaminomethyl, cycloalkylaminomethyl, di-lower alkylaminomethyl, cyclic aminomethyl, acetoxy, acetylamino, lower alkoxymethyl, omega hydroxy lower alkylaminomethyl, cyanomethyl and $R_4$ is hydroxy, acetoxy, cyano, nitro, amino, halo, formyl, lower alkoxy, carbamoyloxy.

A compound wherein each of $R_2$, $R_3$, $R_5$ and $R_6$ is hydrogen and $R_4$ is —OC(O)Alkyl$_{1-20}$.

A compound of Formula (I) wherein $R_{12}$ is lower alkyl, cyano, hydroxycarbonyl, lower alkoxycarbonyl, cycloalkyl, alkylcarbonylamino, 1-napthyl, 2-napthyl or phenyl and $R_{13}$ is hydrogen. Preferably, $R_{12}$ is lower alkyl, cycloalkyl, 1-napthyl, 2-napthyl or phenyl, more preferably, $R_{12}$ is lower alkyl or phenyl.

A compound of Formula (I) wherein $R_{12}$ is hydrogen and $R_{13}$ is lower alkyl, cyano, hydroxycarbonyl, lower alkoxycarbonyl, cycloalkyl, alkylcarbonylamino, 1-napthyl, 2-napthyl or phenyl. Preferably, $R_{13}$ is lower alkyl, cycloalkyl, 1-napthyl, 2-napthyl or phenyl, more preferably, $R_{13}$ is lower alkyl or phenyl.

A compound of Formula (I) wherein $R_{12}$ and $R_{13}$ are hydrogen, lower alkyl, cyano, hydroxycarbonyl, lower alkoxycarbonyl, cycloalkyl, alkylcarbonylamino, 1-napthyl, 2-napthyl or phenyl. Preferably, $R_{12}$ and $R_{13}$ are hydrogen, lower alkyl, cycloalkyl, 1-napthyl, 2-napthyl or phenyl, more preferably, $R_{12}$ and $R_{13}$ are hydrogen, lower alkyl or phenyl.

Pharmaceutical Composition of the Invention

This aspect of the invention is a pharmaceutical composition useful for treating cancer in a warm-blooded animal, which composition comprises compound of the invention as defined herein in combination with a pharmaceutically acceptable excipient. The composition is prepared in accordance with known formulation techniques to provide a composition suitable for oral, topical, transdermal, rectal, by inhalation, parenteral (intravenous, intramuscular, or intraperitoneal) administration, and the like. Detailed guidance for preparing compositions of the invention are found by reference to the $18^{th}$ or $19^{th}$ Edition of Remington's Pharmaceutical. Sciences, Published by the Mack Publishing Co., Easton, Pa. 18040. The pertinent portions are incorporated herein by reference.

Unit doses or multiple dose forms are contemplated, each offering advantages in certain clinical settings. The unit dose would contain a predetermined quantity of active compound calculated to produce the desired effect(s) in the setting of treating cancer. The multiple dose form may be particularly useful when multiples of single doses, or fractional doses, are required to achieve the desired ends. Either of these dosing forms may have specifications that are dictated by or directly dependent upon the unique characteristic of the particular compound, the particular therapeutic effect to be achieved, and any limitations inherent in the art of preparing the particular compound for treatment of cancer.

A unit dose will contain a therapeutically effective amount sufficient to treat cancer in a subject and may contain from about 1.0 to 1000 mg of compound, for example about 50 to 500 mg.

The compound will preferably be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will preferably contain about 50 to about 500 mg of a compound of Formula (I).

The form may deliver a compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. Preferred compositions according to the current invention are prepared so that an oral dosage unit form contains between about 5.0 to about 50% by weight (% w) in dosage units weighing between 5 and 1000 mg.

The suitable formulation of an oral dosage unit may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91–93 for a fuller discussion.

A compound may be administered parenterally, e.g., intravenously, intramuscularly, intravenously, subcutaneously, or interperitonieally. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of the compound may be prepared in suitable diluents such as water, ethanol, glycerol, liquid polyethylene glycol(s), various oils, and/or mixtures thereof, and others known to those skilled in the art.

The pharmaceutical forms suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Although the compounds of this invention tend to be water soluble, in some cases, e.g., where a compound of the invention is less water soluble, it may be useful to provide liposomal delivery. The system restrains the compound of the invention by incorporating, encapsulating, surrounding, or entrapping the compound of the invention in, on, or by lipid vesicles or liposomes, or by micelles.

Liposomes have been used successfully to administer medications to cancer patients, and have been shown to be useful clinically in the delivery of anticancer drugs such as doxorubicin, daunorubicin, and cisplatinum complexes. Forssen, et al., *Cancer Res.* 1992, 52: 3255–3261; Perex-Soler, et al., *Cancer Res.* 1990, 50: 4260–4266; and, Khokhar, et al., *J. Med. Chem.* 1991, 34: 325–329, all of which are incorporated herein in their entireties by reference.

Similarly, micelles have also been used to deliver medications to patients, (Broden et al., *Acta Pharm Suec.* 19: 267–284 (1982)) and micelles have been used as drug carriers and for targeted drug delivery, (D. D. Lasic, *Nature* 335: 279–280 (1992); and, Supersaxo et al., *Pharm Res.* 8: 1280–1291 (1991)), including cancer medications, (Fung et al., *Biomater. Artif. Cells. Artif. Organs* 16: 439 et seq. (1988); and Yokoyama et al., *Cancer Res.* 51: 3229–3236 (1991)), al of which are incorporated herein in their entireties by reference.

The liposomes and/or micelles containing the compound of the invention can be administered to a cancer patient, typically intravenously. Further guidance for preparing liposomal compositions useful in this invention may be found in U.S. Pat. No. 6,096,336, which is incorporated herein by reference.

Method of Treatment of the Invention

Another aspect of this invention is a method for treating cancer in a warm-blooded animal, which method comprises administering a therapeutically effective amount of a compound of the invention as defined herein. A compound useful in this invention is administered to an appropriate subject in need of these compounds in a therapeutically effective dose by a medically acceptable route of administration such as orally, parentally (e.g., intramuscularly, intravenously, subcutaneously, interperitoneally), transdermally, rectally, by inhalation and the like.

The term cancer is to be considered in the broadest general definition as a malignant neoplasm, an abnormal mass of tissue, the growth of which exceeds and is uncoordinated with that of normal tissues and persists in the same excessive manner after cessation of the stimuli that evoked the change. It might be added that the abnormal mass is purposeless, preys on the host, and is virtually autonomous. A cancer can also be considered as a malignant tumor. A further discussion of neoplasia is found at "Robbins Pathologic Basis of Disease," Sixth Edition, by R. S. Cotran, V. Kumar, and T. Collins, Chapter 8 (W. B. Saunders Company). This information from Chapter 8 is incorporated herein by reference. The following Table A provides examples of the types of cancers, i.e., malignant tumors or neoplasia that may be treated by administering a compound of this invention.

TABLE A

| Tissue of Origin | Malignant |
| --- | --- |
| Composed of One Parenchymal Cell Type Mesenchymal tumors | |
| Connective tissue and derivatives | Fibrosarcoma Liposarcoma Chondrosarcome Osteogenic sarcoma |
| Endothelial and related tissues | |
| Blood vessels | Angiosarcoma |
| Lymph vessels | Lymphangiosarcoma |
| Synovium | Synovial sarcoma |
| Mesothelium | Mesothelioma |
| Brain coverings | Invasive meningioma |
| Blood cells and related cells | |
| Hematopoietic cells | Leukemias |
| Lymphoid tissue | Malignant lymphomas |
| Muscle | |
| Smooth | Leiomyosarcoma |
| Straited | Rhabdomyosarcoma |
| Epthelial tumors | |
| Stratified squamous | Squamous cell or epidermoid carcinoma |
| Basal cells of skin or adnexa Epithelial lining | Basal cell carcinoma |
| Glands or ducts | Adenocarcinoma Papillary carcinoma Cystadenocarcinoma |
| Respiratory passages | Bronchogenic carcinoma Bronchial adenoma (carcinoid) |
| Neuroectoderm | Malignant melanoma |
| Renal epithelium | Renal cell carcinoma |
| Liver cells | Hepatocellular carcinoma |
| Urinary tract epithelium (transitional) | Transitional cell carcinoma |
| Placental epithelium (trophoblast) | Choriocarcinoma |
| Testicular epithelium (germ cells) | Seminoma Embryonal carcinoma |
| More Than One Neoplastic Cell-Mixed Tumors, Usually Derived From One Germ Layer | |
| Salivary glands | Malignant mixed tumor of salivary gland origin |
| Breast | Malignant cystosarcoma phyllodes |
| Renal anlage | Wilms tumor |
| More Than One Neoplastic Cell Type Derived From More Than One Germ Layer-Teratogenous | |
| Totipotential cells in gonads or in embryonic rests | Immature teratoma, teratocarcinoma |

The compounds of the invention are thus useful in the treatment of leukemia and solid tumors, such as colon, colo-rectal, ovarian, mammary, prostate, lung, kidney and also melanoma tumors. The dosage range adopted will depend on the route of administration and on the age, weight and condition of the patient being treated. The compounds may be administered, for example, by the parenteral route, for example, intramuscularly, intravenously or by bolus infusion.

As used herein, a "therapeutically effective amount" of hCPT derivatives of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on mg/m² of body surface) is described by E. J. Freireich et al., *Cancer Chemother. Rep.*, 50(4):219 (1966). Body surface area may be approximately determined from the height and weight of an individual (see, e.g., Scientific Tables, Geigy Pharmaceuticals, Ardsley, N.Y. pp. 537–538 (1970)). A suitable dose range is from 1 to 1000 mg of equivalent per m² body surface area of a compound of the invention, for instance from 50 to 500 mg/m².

For all of the administering routes, the exact timing of administration of the dosages can be varied to achieve optimal results. Generally, if using Intralipid 20 as the carrier for the hCPT derivative, the actual dosage of hCPT derivative reaching the patient will be less. This is due to some loss of the hCPT derivative on the walls of the syringes, needles and preparation vessels, which is prevalent with the Intralipid 20 suspension. When a carrier, such as cottonseed oil is used, this above described loss is not so prevalent because the hCPT derivative does not adhere as much to the surface of syringes, etc.

Another important feature of the method provided by the present invention relates to the relatively low apparent overall toxicity of the hCPT derivatives administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

Process of the Invention

Another aspect of this invention is process for preparing compounds of this invention by reacting camptothecin (HCPT) or a HCPT analog with a compound of the formula R—C(O)X, wherein R is $R_aR_bN(CH_2)_m$, $R_a$ and $R_b$ are as defined herein, and X is e.g., bromide, chloride, hydroxy, alkoxy of 1–11 carbons (e.g., —O(CH$_2$)$_n$CH$_3$ where n is an integer of 1–10) or R—C(O)O—(R is defined hereinbefore). Preferably X is OH. The compound shown as $R_aR_bN(CH_2)_mC(O)X$ can be referred to as an aminoalkanoic acid or aminoalkanoic acid derivative, e.g., where m is 2, it is an "aminopropionic acid" or an "aminopropionic acid derivative." One way that such an aminoalkanic acid (e.g., aminopropionic acid) is obtained is by reacting an appropriate amino $R_aR_bNH$ or the imido $R_aR_bNH$ (or their acid addition salt) with an omega-halosubstituted alkanoic acid (e.g., 3-halopropionic ester), then hydrolyzing the ester to form the acid. Examples of preferred halopropionic acid esters include the ethyl ester of 3-bromopropionic acid, 3-chloropropionic acid, or 3-iodopropionic acid. Other corresponding alkyl esters (e.g., methyl, propyl, and the like, are useful but ethyl is preferred). The ethyl ester of 3-bromopropionic acid is preferred. In some cases, it may be useful to prepare an acid halide from the corresponding aminopropionic acid. The acid halides are obtained by reacting the corresponding aminopropionic acid with halogenated agents (such as $SOCl_2$, $PCl_3$, $POCl_3$, $PCl_5$, $PBr_3$, and so on). The acid chloride is preferred. Once the acid or its derivative is prepared, it is reacted with HCPT to form the C-20-ester of HCPT, i.e., compounds of this invention. This reaction sequence can be generalized as follows:

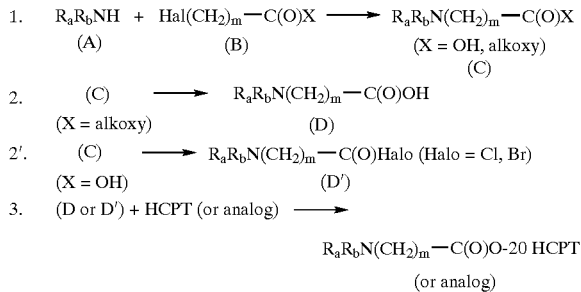

In step 1 the reaction conditions will vary depending on the exact reactants employed. In general, solvents useful in the reaction may be aqueous or nonaqueous. Preferably, a solvent will be a polar organic solvent miscible with water such as a lower alkanol (ethanol is preferred). Examples of other useful polar solvents include methanol, propanol, acetone, and dimethyformamide (DMF). The reaction will generally take place in the presence of an alkaline salt such as sodium bicarbonate. The reaction temperature will vary with the reactant, and the solvents, and will range from about 20° C. to about 180° C., preferably at reflux temperature until the free amine disappears, i.e., it is not detected anymore. The time needed for the reaction to be complete will generally be no more than about 20 hours, preferably no more than about 6 hours.

In step 2, the compound of formula (C) is converted to a compound of formula (D) by a hydrolysis reaction, generally performed in two stages. The reaction conditions for this step will vary in accordance with the compound being reacted. In general, solvents useful in the conversion may be aqueous, preferably, a solvent will be water, either alone or with a water-miscible organic solvent. An example of a particularly useful solvent is a mixture of water and dioxane. The pH of the first stage of reaction will be basic, e.g., in the range of 10 to 14, preferably about 12 to 14. A suitable inorganic base such as an alkaline earth hydroxide, e.g., sodium hydroxide, is useful. The reaction temperature will range from about 0° C. to about 60° C., preferably about 20° C. to about 25° C. The time needed for the reaction to be complete will generally be no more than 10 hours, preferably no more than about 4 hours. The mixture is then acidified to a pH of less than 4, e.g., 3, with an appropriate acid such as hydrochloric acid and extracted, if needed, with a suitable solvent such as ethyl acetate in accordance with standard chemical synthetic methods. Often the resulting propionic acid precipitates as a solid and is filtered off.

In step 2', the compound of formula C (i.e., the aminopropionic acid) is converted into the corresponding acid halide by reacting with a halogenated agent such as $SOCl_2$, $PCl_3$, $POCl_3$, $PCl_5$, $PBr_3$, and the like under appropriate conditions.

In step 3 of the process a compound of formula (D) or (D') is reacted with hCPT or a hCPT analog in about equimolar amounts up to about a 4:1 ratio (D or D':hCPT) under conditions suitable for the formation of the compounds of this invention as the 20-(S) stereoisomer. The reaction takes place in the presence of suitable coupling agent such as a carbodiimide compound, e.g., disopropylcarbodiimide, but preferably 1-(3-dimethylaminopropyl)-3-ethyl carbodiimide hydrochloride (EDCI) and 4-(dimethylamino)pyridine (DMAP) in the presence of a suitable solvent, preferably a nonaqueous, nonpolar solvent. The coupling agent is present in an amount sufficient to aid the process going forward. The amount of the coupling agent is more than is usually needed to drive the reaction forward. The molar amount of DMAP is about 1–2 times or more of the molar amount of the hCPT compound used, while the amount of EDCI is about 5–7 (preferably about 6) times the molar amount of the hCPT compound used. Examples of useful solvents in this step include halogenated alkanes, e.g., dichoromethane or trichloromethane) and DMF. Dichloromethane is particularly useful. The reaction temperature will range from about 20° C. to about 40° C., preferably about 20° C. to about 25° C. The time needed for the reaction to be complete will generally be no more than about 20 hours, usually less than about 10 hours. It should be noted that a compound of formula (I) wherein one of $R_2$–$R_6$ is $R_aR_bN(CH_2)$—C(O)O— along with R being $R_aR_bN(CH_2)_2$ is obtained by reacting an analog where one of $R_2$–$R_6$ (particularly $R_4$) is a hydroxy. In this case, the compound (e.g., the 10 hydroxy hCPT), is reacted with 2 molar equivalents of the aminopropionic acid to give the disubstituted hCPT derivative.

An alternative process for preparing preferred compounds of this invention involve starting with a suitable anhydride and converting it to an imidopropionic acid, which is in turn reacted with hCPT or a hCPT analog to give a compound of the invention in accordance with Step 3 of the reaction sequence above. This anhydride conversion can be visualized as follows:

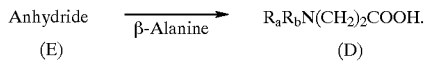

$$\text{Anhydride} \xrightarrow{\beta\text{-Alanine}} R_aR_bN(CH_2)_2COOH.$$
$$(E) \qquad\qquad\qquad (D)$$

Generally the anhydride is reacted with β-alanine in the presence of a suitable solvent and a catalyst. Suitable solvents include polar, water-miscible solvents, such as alcohols, acetone, dioxane, and the like. Ethanol is preferred. A suitable catalyst is dimethylaminopyridine (DMAP). Generally, the reaction is carried out at reflux temperature for less than 10 hours, e.g., about three. Adding water results in the precipitation of the compound, which is then dried to give the resulting imidopropionic acid designated as (D). This compound is then reacted with hCPT or a hCPT analog to give a compound of this invention.

In step 1, of the reaction sequence above, suitable amines represented by formula (A) include the following:

1-(3-trifluoromethyl)phenylpiperazine;
1-(4-benzyl)piperazine;
1-[4-(3-methoxyphenyl)]piperazine;
1-[4-(4-nitrophenyl)]piperazine;
1-(4-phenyl)piperazine;
1-[4-(2-chlorophenyl)]piperazine (as the HCl salt);
1-[4-(4-fluorophenyl)]piperazine;
3-[4-(4-acetylphenyl)piperazine;
4-benzylpiperidine;
piperidine;
piperazine;
morpholine; and the like.

One of skill in the art will recognize other representative amines with the guidance of this specification.

In step 2, suitable 3-cyclicaminopropionic acid esters represented by formula (C) include the following:

ethyl 3-[4-(3-trifluoromethylphenyl)-1-piperazinyl]propionate;
ethyl 3-(4-benzyl-1-piperazinyl)propionate;
ethyl 3-[4-(4-nitrophenyl)-1-piperazinyl]propionate;
ethyl 3-(4-phenyl-1-piperazinyl)propionate;
ethyl 3-[4-(2-chlorophenyl)-1-piperazinyl]propionate;
ethyl 3-[4-(4-fluorophenyl)-1-piperazinyl]propionate;
ethyl 3-(4-benzyl-1-piperidino)propionate;
ethyl 3-[4-(4-acetylphenyl)-1-piperazinyl]propionate; and the like.

In step 3, a suitable hCPT analogue is a compound that is hCPT substituted at the 7, 9, 10, 11, 12 or 22 positions as described in this document. The hCPT analogue may be substituted with substituents known in the art or that can be prepared by one of skill in the art given the disclosure herein (i.e., from CPT analogues). Representative articles that teach how to make CPT analogues or where such analogues may be procured are found in the following journals (which are incorporated herein by reference).

1. *J. Med. Chem.* 1998, 41, 31–37
2. *J. Med. Chem.* 2000, 43, 3970–3980
3. *J. Med. Chem.* 1993, 36, 2689–2700
4. *J. Med. Chem.* 1991, 34, 98–107
5. *J. Med. Chem.* 2000, 43, 3963–3969
6. *Chem. Pharm. Bull.* 39(10) 2574–2580 (1991)
7. *Chem. Pharm. Bull.* 39(6) 1446–1454 (1991)
8. ANTIMICROBIAL AGENTS AND CHEMOTHERAPY, December 1999, p. 2862–2868
9. *European Journal of Cancer*, Vol. 34, No. 10, pp. 1500–1503, 1998
10. CANCER RESEARCH 55, 753–760, Feb. 15, 1995
11. *Anti-Cancer Drug Design* (1998), 13, 145–157
12. Bioorganic & Medicinal Chemistry Letters 8 (1998) 415–418
13. CANCER RESEARCH 61, 6034–6037, Aug. 15, 2001
14. *Clinical Cancer Research* 2002, 8, 641–661

Suitable CPT analogs include the following, where the number in parenthesis following the name refers to journal article listed above:

camptothecin (CPT);
exatecan mesylate (14-AKA DX8951f)
(20S)-7-ethyl-10-[4-(1-piperidino)-1-piperidino]carbonyloxy)-CPT (AKA-irinotecan);
(20S)-9-nitro CPT (1);
(20S)-7-chloro-n-propyldimethylsilyl CPT (2);
(20S)-10-hydroxy-7-chloro-n-propyldimethylsilyl CPT (2);
(20S)-10-acetoxy-7-chloro-n-propyldimethylsilyl CPT (2);
(20S)-7-tert-butyldimethylsilyl CPT (2);
(20S)-10-hydroxy-7-tert-butyldimethylsilyl CPT (2);
(20S)-10-acetoxy-7-tert-butyldimethylsilyl CPT (2);
(20S)-9-hydroxy CPT (3);
(20S)-9-amino CPT (3);
(20S)-10-amino CPT (3);
(20S)-9-amino-10-hydroxy CPT (3);
(20S)-9-amino-10,11-methylenedioxy CPT (3);
(20S)-9-methylamino CPT;
(20S)-9-methyl CPT (3);
(20S)-9-dimethylamino CPT;
(20S)-9-chloro CPT (3);
(20S)-9-trimethylsilylethyl CPT (14-AKA Karenitecin);
(20S)-7-(4-methylpiperazinomethylene)-10,11-ethylenedioxy CPT (14)

(20S)-9-dimethylaminomethyl-10-hydroxy CPT (3-AKA topotecan);
(20S)-9-fluoro CPT (3);
(20S)-9-piperidino CPT;
(20S)-9-dimethylaminomethyl-10-hydroxy CPT (3);
(20S)-9-morpholinomethyl CPT (4);
(20S)-10-hydroxy CPT (3);
(20S)-9,10-dichloro CPT (3);
(20S)-10-bromo CPT (3);
(20S)-10-chloro CPT (3);
(20S)-10-methyl CPT (3);
(20S)-10-fluoro CPT (3);
(20S)-10-nitro CPT (3);
(20S)-10,11-methylenedioxy CPT (3);
(20S)-10-formyl CPT (3);
(20S)-10-nonylcarbonyloxy CPT (12);
(20S)-10-undecylcarbonyloxy CPT (12);
(20S)-10-pentadecylcarbonyloxy CPT.(12);
(20S)-10-heptadecylcarbonyloxy CPT (12);
(20S)-10-nonadecylcarbonyloxy CPT (12);
(20S)-9-nitro-10,11-methylenedioxy CPT (3);
(20S)-9-(4-methylpiperazinylmethyl)-10-hydroxy (CPT) (4);
(20S)-9-[4-(1-piperidino)-1-piperidinomethyl]-10-hydroxy CPT (4);
(20S)-9-methyl-10,11-methylenedioxy CPT;
(20S)-9-chloro-10,11-methylenedioxy CPT (3);
(20S)-9-cyano-10,11-methylenedioxy CPT;
(20S)-9-acetoxy-10,11-methylenedioxy CPT;
(20S)-9-acetylamino-10,11-methylenedioxy CPT;
(20S)-9-aminomethyl-10-hydroxy CPT;
(20S)-9-ethoxymethyl-10-hydroxy CPT (4);
(20S)-9-methylaminomethyl-10-hydroxy CPT;
(20S)-9-n-propylaminomethyl-10-hydroxy CPT (4);
(20S)-9-dimethylaminomethyl-10-hydroxy CPT (4);
(20S)-9-cyclohexylaminomethyl-10-hydroxy CPT (4);
(20S)-9-(2-hydroxyethyl)aminomethyl-10-hydroxy CPT (4);
(20S)-9-(trimethylammonio)methyl-10-hydroxy CPT, methanesulfonate (4);
(20S)-9-morpholinomethyl-10-hydroxy CPT (4);
(20S)-9-cyanomethyl-10-hydroxy CPT (4);
(20S)-CPT-7-aldehyde (5);
(20S)-10-methoxy CPT-7-aldehyde (5);
(20S)-7-acetoxymethyl CPT (5);
(20S)-7-acetoxymethyl-10-methyl CPT (5);
(20S)-7-cyano-10-methoxy CPT (5);
(20S)-7-cyano CPT (5);
(20S)-7-formylethenyl CPT (5);
(20S)-7-ethoxycarbonylethenyl CPT (5);
(20S)-7-cyanoethenyl CPT (5);
(20S)-7-(2,2-dicyanoethenyl) CPT (5);
(20S)-7-(2-cyano-2-ethoxycarbonyl)ethenyl CPT (5);
(20S)-7-ethoxycarbonylethyl CPT (5);
(20S)-7-ethyl CPT (6);
(20S)-7-n-propyl CPT (6);
(20S)-7-acetoxymethyl CPT (6);
(20S)-7-n-propylcarbonyloxymethyl CPT (6);
(20S)-7-ethoxycarbonyl CPT (6);
(20S)-7-ethyl-10-hydroxy CPT;
(20S)-7-ethyl-10-acetyloxy CPT;
(20S)-7-methyl-10-aminocarbonyloxy CPT;
(20S)-7-n-propyl-10-piperidinocarbonyloxy CPT;
(20S)-7-ethyl-10-(2-dimethylamino)ethyl CPT; and
(20S)-7-ethyl-10-carbamoyloxy derivatives of CPT such as
(20S)-7-ethyl-10-[4-(1-piperidino)-piperidino carbonyloxy CPT (7);
(20S)-7-ethyl-10-(1-piperazine)carbonyloxy CPT (7);
(20S)-7-ethyl-10-(4-i-propylaminocarbonylmethylpiperazine)carbonyloxy CPT (7);
(20S)-7-ethyl-10-[4(1-pyrrolidinyl)piperazine] carbonyloxy CPT (7);
(20S)-7-ethyl-10-[(4-(dimethylamino)-1-piperidino] carbonyloxy CPT (7);
(20S)-7-ethyl-10-[4-(di-n-propylamino)-1-piperidinol] carbonyloxy CPT (7);
(20S)-7-ethyl-10-[(4-(di-n-butylamino)-1-piperidino] carbonyloxy CPT (7);
(20S)-7-ethyl-10-[4-(1-pyrrolidino)-1-piperidino)] carbonyloxy CPT (7);
(20S)-7-butoxyiminomethyl CPT;
(20S)-7-ethyl-10-[4-(1-piperidino)-1-piperidino] carbonyloxy CPT (7);
(20S)-7-ethyl-10-[N-methyl-N-2-(dimethylamino) ethylamino]carbonyloxy CPT (7) and the like.

CPT and CPT analogues (listed above) may be converted to hCPT and hCPT analogues by the following partial synthesis illustrated for CPT (Lavergne et al., Ann. N.Y. Acad. Sci. 2000, 922: 100–111).

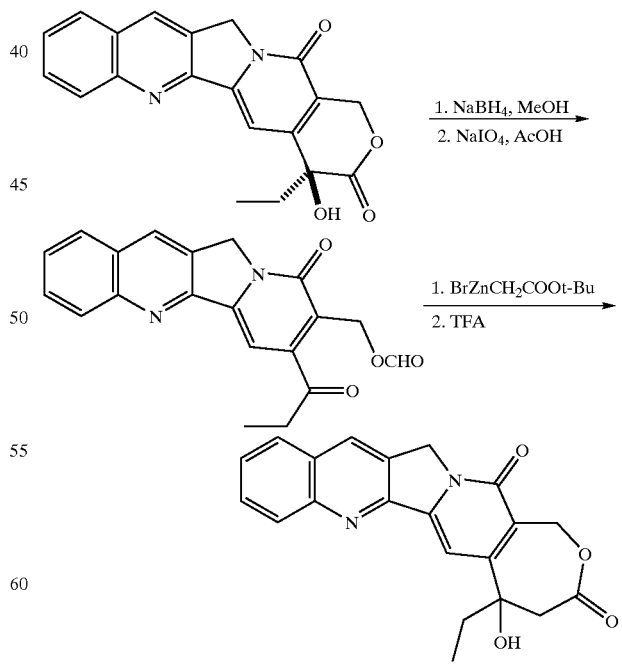

Alternatively, total synthesis of hCPT analogues may be performed by analogy to the procedure described in Lavergne et al., Ann. N.Y. Acad. Sci. 2000, 922: 100–111.

It will be recognized by one of skill in the art that other similar compounds may be prepared by following the teachings set forth in the above articles and modifying with appropriate art-recognized steps.

In step 3, suitable 3-aminopionic acids of formula (D) including the following:

3-phthalimidopropionic acid;
3-maleimidopropionic acid;
3-(3-nitro 1,8-naphthalimide)propionic acid;
3-(4-nito-1,8-naphthalimide)propionic acid;
3-(4-bromo-1,8-naphthalimido)propionic acid;
3-[4-(3-trifluoromethylphenyl)-1-piperazinyl]-propionic acid;
3-[(4-benzyl)-1-piperazinyl]propionic acid;
3-[4-(3-methoxyphenyl)-1-piperazinyl]propionic acid;
3-[4-(4-nitrophenyl)-1-piperazinyl]propionic acid;
3-(4-phenyl-1-piperazinyl)propionic acid;
3-[4-(2-chlorophenyl)-1-piperazinyl]propionic acid;
3-[4-(4-fluorophenyrl)-1-piperazinyl]propionic acid;
3-(1-piperidino)propionic acid;
3-[1-(4-benzyl)piperidino]propionic acid;
3-[4-(4-acetylphenyl-1-piperazinyl]propionic acid;
3-[4-(3,4-dichlorophenyl)-1-piperazinyl]propionic acid;
3-[4-(3,4-methylenedioxyphenyl)-1-piperazinyl] propionic acid;
3-[4-(4-chlorophenyl)-1-piperidinyl]propionic acid;
3-(4-formyl-1-piperazinyl)propionic acid;
3-(4-ethyl-1-piperazinyl)propionic acid;
3-[4-(4-chlorophenyl)phenylmethyl-1-piperazinyl] propionic acid;
3-(4-cyano-4-phenyl-1-piperidinyl)propionic acid;
3-trans-4-cinnamyl-1-piperazinyl)propionic acid;
3-[4-(2-methylphenyl)-1-piperazinyl]propionic acid;
3-[4-(2,3-dimethylphenyl)-1-piperazinyl]propionic acid;
3-[4-(1-piperidino)-1-piperidino]propionic acid;
3-[4-(2-pyrimidinyl)-1-piperazinyl]propionic acid;
3-(4-cyclohexyl-1-piperazinyl)propionic acid;
3-[4-(α-(2-pyridyl)benzyl-1-piperazinyl]propionic acid;
3-(4-morpholino)propionic acid;
3-(1-pyrrolinyl)propionic acid;
4-[4-(3-trifluoromethylphenyl)-1-piperazinyl]butyric acid;
5-[4-(3-trifluoromethylphenyl)-1-piperazinly]valeric acid; and the like.

One of skill in the art will recognize that other similar 3-aminopropionic acids may be obtained from commercial sources or prepared by art-recognized procedures to be used in step 3 to prepare compounds of this invention. By reacting a compound shown in the list of hCPT analogs with a compound shown in the list of compounds of formula (D) in accordance with the guidelines for reaction condition, compounds of the invention will be obtained. These compounds will exhibit the desired charcteristics to a greater or lesser extent. Guidance is provided herein as to the preferred subgroups of compounds within the family.

EXAMPLES

The following examples are given to provide representative compounds included as part of this invention. The examples also provide descriptions of in vitro and in vivo assays to aid in determining the utility of the compounds. The homo-camptothecin esters in examples 1–15 were prepared by the corresponding aminopropionic acid and homo-camptothecin. Throughout the examples chemical formulas will be used to name compounds (e.g., $NaHCO_3$ is sodium bicarbonate) as appropriate. In naming the compounds, generally two approaches are used. One approach used in the section heading of each example is to refer to the compound as the homo-camptothecin C-20-ester of the propionic acid. The other approach used is to refer to the compound as the homo-camptothecin-20-O-3-propionate. Each approach is meant to name the same compound. E.g., in Example 1, the homo-camptothecin-20-ester of 3-phthalimidopropionic acid is the same compound as homo-camptothecin-20-O-3-phthalimidopropionate.

Example 1

This example explains how to prepare non-substituted and substituted homo-camptothecin-20-esters of 2-phthalimidopropionic acid.

A. Homo-camptothecin-20-ester of 3-phthalimidopropionic Acid

The mixture of homo-camptothecin (0.029 mmol), 3-phthalimidopropionic acid (12.7 mg, 0.058 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. The organic layer is washed with water (20 ml), saturated $NaHCO_3$ aqueous solution (10 ml) and brine (20 ml), and then dried over $MgSO_4$. After the solvent is removed under reduced pressure, the resulting solid is separated by column chromatography to afford homo-camptothecin-20-O-3-phthalimidopropionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Note that "homo irinotecan" is the hCPT derivative obtained from irinotecan and that "homo topotecan" is the hCPT derivative obtained from topotecan in this and other examples. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;

9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 2

This example explains how to prepare non-substituted and substituted homo-camptothecin-20-esters of 3-maleimidopropionic acid.

A. Homo-camptothecin-20-ester of 3-maleimidopropionic Acid

The mixture of homo-camptothecin (0.029 mmol), 3-maleimidopropionic acid (10 mg, 0.059 mmol), EDCI (25 mg, 0.17 mmol), DMAP (2 mg, 0.038 mmol) and dichloromethane (3 ml) is stirred at room temperature for 20 h, then dichloromethane (20 ml) is added to the solution. The organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-maleimidopropionate, mp 243–245° C.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 3

This example explains how to prepare non-substituted and substituted homo-camptothecin-20-esters of 3-(3-nitro-1,8-naphthalimide)propionic acid.

A. Homo-camptothecin-20-ester of 3-(3-nitro-1,8-naphthalimide)propionic Acid

1. Synthesis of 3-(3-nitro-1,8-naphthalimide)propionic Acid

The reaction mixture of 3-nitro-1,8-naphthalic anhydride (243 mg, 1.0 mol), β-alanine (90 mg, 1.0 mol), DMAP (10 mg, 0.1 mmol) and ethanol (15 ml) was refluxed for 3 h. Then 15 ml of water was added. The mixture is filtered, and the solid was washed with water, and then dried in the oven to give 224 mg 3-(3-nitro-1,8-naphthalimide)propionic acid as a gray solid, mp 250–255° C.

The chemical structure analysis was performed by $^1$HNMR (DMSO-d$_6$, 600 MHz): δ 9.39 (d, 1H, Ar—H), 8.85 (d, 1H, Ar—H), 8.70 (d, 1H, Ar—H), 8.61 (d, 1H, Ar—H), 8.00 (t, 1H, Ar—H) 4.25 (t, 2H, NCH$_2$), 2.62 (t, 2H, COCH$_2$).

2. Synthesis of homo-camptothecin-20-0-[3-(3-nitro-1,8-naphthalimide)propionate]

A mixture of homo-camptothecin (0.027 mmol), 3-(3-nitro-1,8-naphthalimide)-propionic acid (18 mg, 0.058 mmol), EDCI (25 mg, 0.16 mmol), DMAP (2 mg, 0.035 mmol), and dichloromethane (3 ml) is stirred at room temperature for 20 h, then dichloromethane (20 ml) is added to the solution. The organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford the title compound.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;

9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 4

This example explains how to prepare non-substituted and substituted homo-camptothecin-20-esters of 3-(4-nitro-1,8-naphthalimide)propionic acid.

A. Homo-camptothecin-20-ester of 3-(4-nitro-1,8-naphthalimide)propionic Acid

1. Synthesis of 3-(4-nitro-1,8-naphthalimide)propionic Acid

The reaction mixture of 4-nitro-1,8-naphthalic anhydride (243 mg, 1.0 mol), β-alanine(125 mg, 1.4 mol), DMAP (10 mg, 0.1 mmol) and ethanol (15 ml) was refluxed for 3 h. Then 15 ml of water was added. The mixture was filtered, and the solid was washed with water, and then dried in the oven to give 227 mg 3-(4-nitro-1,8-naphtalimide)propionic acid.

The chemical structure analysis was performed by $^1$HNMR (DMSO-$d_6$, 600 MHz): δ 8.69 (t, 1H, Ar—H), 8.60 (m, 2H, Ar—H), 8.54 (d, 1H, Ar—H), 8.08 (t, 1H, Ar—H), 4.25 (t, 2H, $NCH_2$), 2.62 (t, 2H, $COCH_2$).

2. Synthesis of homo-camptothecin-20-O-13-(4-nitro-1,8-naphthalimide)propionate]

The mixture of homo-camptothecin (0.029 mmol), 3-(4-nitro-1,8-naphthalimide)-propionic acid (13 mg, 0.041 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated $NaHCO_3$ aqueous solution (10 ml) and brine (20 ml), and then dried over $MgSO_4$. After the solvent is removed under reduced pressure, the resulting solid is separated by column chromatography to afford homo-camptothecin-20-O-[3-(4-nitro-1,8-naphthalimide) propionate].

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 5

This example explains how to prepare non-substituted and substituted homo-camptothecin-20-ester of 3-(4-bromo-1,8-naphthalimide)propionic acid.

A. Homo-camptothecin-20-ester of 3-(4-bromo-1,8-naphthalimide)propionic Acid

1. Synthesis of 3-(4-bromo-1,8-naphthalimide)propionic Acid

The reaction mixture of 4-bromo-1,8-naphthalic anhydride (277 mg, 1.0 mol), β-alanine (120 mg, 1.3 mol), DMAP (10 mg, 0.1 mmol) and ethanol (15 ml) was refluxed for 4 h. The mixture was filtered, and the solid s washed with ethanol, and then dried in the oven to give 300 mg 3-(4-bromo-1,8-naphthalimide)propionic acid as a gray solid, mp 220–225° C.

The chemical structure analysis was performed by $^1$HNMR (DMSO-$d_6$, 600 MHz): δ 8.58 (t, 2H, Ar—H), 8.35 (d, 1H, Ar—H), 8.24 (d, 1H, Ar—H), 8.01 (t, 1H, Ar—H), 4.25 (t, 2H, $NCH_2$), 2.59 (t, 2H, $COCH_2$).

2. Synthesis of homo-camptothecin-20-O-[3-(4-bromo-1,8-naphthalimide)propionate]

The mixture of homo-camptothecin (0.029 mmol), 3-(4-bromo-1,8-naphthalimide)propionic acid (19 mg, 0.056 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated $NaHCO_3$ aqueous solution (10 ml) and brine (20 ml), and then dried over $MgSO_4$. After the solvent is removed under reduced pressure, the resulting solid was separated by column chromatography to afford homo-camptothecin-20-O-[3-(4-bromo-1,8-naphthalimide) propionate].

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 6

This example explains how to prepare non-substituted and substituted homo-camptothecin-20-esters of 3-[4-(3-trifluoromethylphenyl)-1 piperazinyl]propionic acid.

A. Homo-camptothecin-20-ester of 3-[4-(3-trifluoromethylphenyl)-1-piperazinyl]-propionic Acid 1. Synthesis of 3-[4-(3-trifluoromethylphenyl)-1-piperazinyl]propionic Acid The reaction mixture of 1-(3-trifluoromethylphenyl) piperazine (510 mg, 2.2 mmol), ethyl 3-bromopropionate (500 mg, 2.7 mmol), sodium bicarbonate (300 mg, 3.5 mmol) and ethanol (15 ml) was refluxed for 3 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 500 mg 3-[4-(3-trifluoromethylphenyl)-1-piperazinyl]propionic acid as a white solid, mp 228–230° C.

The chemical structure analysis was performed by $^1$HNMR (DMSO-$d_6$, 600 MHz): δ 7.47 (t, 1H, Ar—H), 7.29 (t, 2H, Ar—H), 7.15 (d, 1H, Ar—H), 3.36 (m, 10H, NCH$_2$), 2.89 (t, 2H, COCH$_2$).

2. Synthesis of homo-camptothecin-20-O-3-[4-(3-trifluoromethylphenyl)-1-piperazinyl]propionate The mixture of homo-camptothecin (10 mg, 0.029 mmol), 3-[4-(3-trifluoromethylphenyl)-1-piperazinyl]propionic acid (19 mg, 0.063 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid was separated by column chromatography to afford homo-camptothecin-20-O-3-[4-(3-trifluoromethylphenyl)-1-piperazinyl]propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 7

This example explains how to prepare non-substituted and substituted homo-camptothecin-20-esters of 3-[(4-benzyl)piperazin-1-yl]propionic acid.

A. Homo-camptothecin-20-ester of 3-1(4-benzyl)-1-piperazinyl]propionic Acid

1. Synthesis of 3-[(4-benzyl)-1-piperazinyl]propionic Acid

The reaction mixture 1-(4-benzyl)piperazine (380 mg, 2.16 mmol), ethyl 3-bromopropionate (500 mg, 2.7 mmol), sodium bicarbonate (300 mg, 3.5 mmol) and ethanol (15 ml) was refluxed for 6 h till the amine disappeared completely .

After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 265 mg 3-[(4-benzyl)-1-piperazinyl]propionic acid, mp 165–166° C.

The chemical structure analysis was performed by $^1$HNMR (DMSO-$d_6$, 600 MHz): δ 7.38 (m, 4H, Ar—H), 3.40–2.60 (m, 14H, NCH$_2$ and COCH$_2$).

2. Synthesis of homo-camptothecin-20-O-3-[(4-benzyl)-1-piperazinyl]propionate

The mixture of homo-camptothecin (0.029 mmol), 3-[(4-benzyl)piperazin-1-yl]propionic acid (14.3 mg, 0.058 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-[(4-benzyl)-1-piperazinyl]propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 8

This example explains how to prepare non-substituted and substituted homo-camptothecin-20-esters of 3-[4-(3-methoxyphenyl)-1-piperazinyl]propionic acid.

A. Homo-camptothecin-20-ester of 3-[4-(3-methoxyphenyl)-1-piperazinyl]propionic Acid 1. Synthesis of 3-[4-(3-methoxyphenyl)-1-piperazinyl]propionic Acid The reaction mixture 1-(4-(3-methoxyphenyl))piperazine (384 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 191 mg 3-[4-(3-methoxyphenyl)-1-piperazinyl]propionic acid, mp 180–183° C.

The chemical structure analysis was performed by $^1$HNMR (DMSO-$d_6$, 600 MHz): δ 10.75 (bs, 1H, COOH), 7.15 (t, 1H, Ar—H), 6.58 (d, 1H, Ar—H), 6.53 (s, 1H, Ar—H), 6.44 (d, 1H, Ar—H), 4.00–3.00 (m, 10H, NCH$_2$), 2.88 (t, 2H, COCH$_2$).

2. Synthesis of homo-camptothecin-20-O-3-[4-(3-methoxyphenyl)-1-piperazinyl]propionate The mixture of homo-camptothecin (0.029 mmol), 3-[4-(3-methoxyphenyl)-1-piperazin-1-yl]propionic acid (15.3 mg, 0.058 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-[4-(3-methoxyphenyl)-1-piperazin-1-yl]propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;

9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloky hCPT;
7-n-propyl-10-piperidinocarbonyloxy hCPT;
7-ethyl-10-(2-dimethylamino)ethyl hCPT; and the like.

Example 9

This example explains how to prepare non-substituted and substituted homo-camptothecin-20-esters of 3-[4-(4-nitrophenyl)-1-piperazinyl]propionic acid.

A. Homo-camptothecin-20-ester of 3-[4-(4-nitrophenyl)-1-piperazinyl]propionic Acid 1. Synthesis of 3-[4-(4-nitrophenyl)-1-piperazinyl] propionic Acid The reaction mixture 1-[4-(4-nitrophenyl)]piperazine (414 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 300 mg 3-[4-(4-nitrophenyl)-1-piperazinyl]propionic acid, mp 250–252° C.

The chemical structure analysis was performed by $^1$HNMR (DMSO-$d_6$, 600 MHz): δ 11.90 (bs, 1H, COOH), 8.11 (d, 2H, Ar—H), 7.14 (d, 2H, Ar—H), 3.34 (t, 10H, NCH$_2$), 2.88 (t, 2H, COCH$_2$).

2. Synthesis of homo-camptothecin-20-O-3-[4-(4-nitrophenyl)-1-piperazinyl]propionate The mixture of homo-camptothecin (0.029 mmol), 3-[4-(4-nitrophenyl)-1-piperazinyl]propionic acid (16 mg, 0.058 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-[4-(4-nitrophenyl)-1-piperazinyl] propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT 7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 10

This example explains how to prepare non-substituted and substituted homo-camptothecin-20-esters of 3-(4-phenyl-1-piperazinyl)propionic acid.

A. Homo-camptothecin-20-ester of 3-(4-phenyl-1-piperazinyl)propionic Acid

1. Synthesis of 3-(4-phenyl-1-piperazinyl)propionic Acid

The reaction mixture of 1-(4-phenyl)piperazine (324 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen-chloride. Solid was filtered and washed with water, and then dried to give 246 mg 3-(4-phenyl-1-piperazinyl)propionic acid, mp 213–215° C.

The chemical structure analysis was performed by $^1$HNMR (DMSO-$d_6$, 600 MHz): δ 7.26 (t, 2H, Ar—H), 7.00 (d, 2H, Ar—H), 6.87 (t, 1H, Ar—H), 3.37 (t, 10H, NCH$_2$), 2.83 (t, 2H, COCH$_2$).

2. Synthesis of homo-camptothecin-20-O-3-(4-phenyl-1-piperazinyl)propionate

The mixture of homo-camptothecin (0.029 mmol), 3-(4-phenylpiperazin-1-yl)propionic acid (13.4 mg, 0.058 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-(4-phenyl-1-piperazinyl)propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 11

This example explains how to prepare non-substituted and substituted homo-camptothecin-20-esters of 3-[4-(2-chlorophenyl)-1-piperazinyl]propionic acid.
A. Homo-camptothecin-20-ester of 3-[4-(2-chlorophenyl)-1-piperazinyl]propionic Acid
1. Synthesis of 3-[4-(2-chlorophenyl)-1-piperazinyl] propionic Acid The reaction mixture 1-[4-(2-chlorophenyl)]piperazine monohydrochloride (466 mg, 2 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 246 mg 3-[4-(2-chlorophenyl)-1-piperazinyl]propionic acid, mp 210–213° C.

The chemical structure analysis was performed by $^1$HNMR ($D_2O$, 600 MHz): δ 7.44 (d, 1H, Ar—H), 7.29 (t, 1H, Ar—H), 7.18 (d, 1H, Ar—H), 7.10 (t, 1H, Ar—H), 3.64–3.08 (m, 10H, $NCH_2$), 2.85 (t, 2H, $COCH_2$).

2. Synthesis of homo-camptothecin-20-O-3-[4-(2-chlorophenyl)-1-piperazinyl]propionate The mixture of homo-camptothecin (0.029 mmol), 3-[4-(2-chlorophenyl)-1-piperazinyl]propionic acid (15 mg, 0.056 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated $NaHCO_3$ aqueous solution (10 ml) and brine (20 ml), and then dried over $MgSO_4$. After the solvent is removed under reduced pressure, the resulting solid is separated by column chromatography to afford homo-camptothecin-20-O-3-[4-(2-chlorophenyl)-1-piperazinyl] propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 12

This example explains how to prepare non-substituted and substituted homo-camptothecin-20-esters of 3-[4-(4-fluorophenyl)-1-piperazinyl]propionic acid.
A. Homo-camptothecin-20-ester of 3-[4-(4-fluorophenyl)-1-piperazinyl]propionic Acid
1. Synthesis of 3-[4-(4-fluorophenyl)-1-piperazinyl] propionic Acid The reaction mixture 1-[4-(4-fluorophenyl)]piperazine (360 mg, 2.0 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 482 mg 3-[4-(4-fluorophenyl)-1-piperazinyl]propionic acid, mp 178–180° C.

The chemical structure analysis was performed by $^1$HNMR (DMSO-d$_6$, 600 MHz): δ 7.09 (d, 2H, Ar—H), 7.04 (t, 2H, Ar—H), 3.40–3.32 (m, 10H, NCH$_2$), 2.91 (t, 2H, COCH$_2$).

2. Synthesis of homo-camptothecin-20-O-3-[4-(4-fluorophenyl)-1-piperazinyl]-propionate The mixture of homo-camptothecin (0.029 mmol), 3-[4-(4-fluorophenyl)-1-piperazinyl]propionic acid (15 mg, 0.056 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-[4-(fluorophenyl)-1-piperazinyl] propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 13

This example explains how to prepare non-substituted and substituted homo-camptothecin-20-O-3-(1-piperidino) propionates.

A. Homo-camptothecin-20-O-3-(1-piperidino)propionate

The mixture of homo-camptothecin (0.029 mmol), 3-(1-piperidino)propionic acid (10 mg, 0.063 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3(1-piperidino)propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 14

This example explains how to prepare non-substituted and substituted homo-camptothecin-20-esters of 3-[1-(4-benzyl)piperidino]propionate.

A. Homo-camptothecin-20-ester of 3-[1-(4-benzyl)piperidino]propionate

1. Synthesis of 3-[1-(4-benzyl)piperidino]propionic acid

The reaction mixture of 4-benzylpiperidine (350 mg, 2.0 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrochloric acid. Solid was filtered and washed with water, and then dried to give 346 mg, 3-[1-(4-benzyl)piperidino]propionic acid, mp 214–215° C.

The chemical structure analysis was performed by $^1$HNMR (DMSO-d$_6$, 600 MHz): δ 7.29 (t, 2H, Ar—H), 7.19 (m, 3H, Ar—H), 3.40 (d, 2H, NCH$_2$), 3.22 (d, 4H, CH$_2$), 2.86 (m, 5H, CH$_2$CH$_2$CO and H4), 2.56 (s, 2H, Ar—CH$_2$), 1.74 (m, 5H, CH$_2$).

2. Synthesis of homo-camptothecin-20-O-3-[1-(4-benzyl)piperidino]propionate

The mixture of homo-camptothecin (0.029 mmol), 3-[1-(4-benzyl)piperidino]propionic acid (14 mg, 0.056 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-[1-(4-benzyl)piperidino]propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 15

This example explains how to prepare non-substituted and substituted homo-camptothecin-20-esters of 3-[4-(4-acetylphenyl)-1-piperazinyl]propionic acid.

A. Homo-camptothecin-20-ester of 3-[4-(4-acetylphenyl)-1-piperazinyl]propionic Acid 1. Synthesis of 3-[4-(4-acetylphenyl)-1-piperazinyl]propionic Acid The reaction mixture 1-[4-(4-acetylphenyl)]piperazine (408 mg, 2.0 mmol), ethyl 3-bromopropionate (500 mg, 2.7 mmol), sodium bicarbonate (300 mg, 3.5 mmol) and ethanol (15 ml) was refluxed for 6 h till the amine disappeared completely. After the mixture was filtered, the resulting solid was dissolved in 5 ml dioxane and 14 ml 5% sodium hydroxide solution. The mixture was stirred at room temperature overnight, then it was acidified with concentrated hydrogen chloride. Solid was filtered and washed with water, and then dried to give 330 mg 3-[4-(4-acetylphenyl)-1-piperazinyl]propionic acid, mp 204–206° C.

The chemical structure analysis was performed by $^1$HNMR (DMSO-d$_6$, 600 MHz): δ 7.86 (d, 2H, Ar—H), 7.07 (d, 2H, Ar—H), 3.40–3.32 (m, 10H, NCH$_2$), 2.82 (t, 2H, COCH$_2$), 2.48 (s, 3H, COCH$_3$).

2. Synthesis of homo-comptothecin-20-O-3-[4-(4-acetylphenyl)-1-piperazinyl]propionate The mixture of homo-camptothecin (0.029 mmol), 3-[4-(4-acetylphenyl)-1-piperazinyl]propionic acid (16 mg, 0.058 mmol), EDCI (25 mg, 0.17 mmol), DMAP (2 mg, 0.038 mmol) and dichloromethane (3 ml) is stirred in the room temperature for 20 h, then dichloromethane (20 ml) is added to the solution. Organic layer is washed with water (20 ml), saturated NaHCO$_3$ aqueous solution (10 ml) and brine (20 ml), and then dried over MgSO$_4$. After the solvent is removed under reduced pressure, the resulting solid is separated by column chromatography to afford homo-camptothecin-20-O-3-[4-(4-acetylphenyl)-1-piperazinyl]propionate.

B. By substituting other homo-camptothecin analogs for homo-camptothecin (hCPT) in part A of this example other compounds of this invention are prepared. In naming hCPT analogs, the standard numbering system for homo-camptothecin will be employed with "hCPT" being used as an abbreviation for homo-camptothecin. Other homo-camptothecin analogs include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy hCPT (homo topotecan);

9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy HCPT;
9-methylaminomethyl-10-hydroxy HCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 16

This example explains how to prepare non-substituted and substituted homo-camptothecin-20-O-esters of 1-piperidine propionic acid.

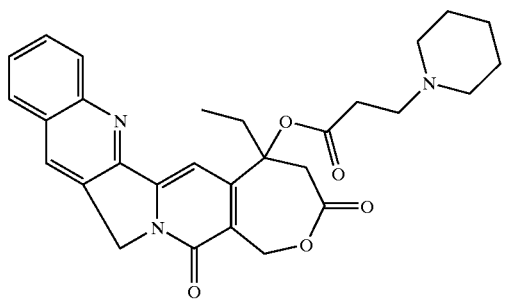

A. Homocamptothecin-20-O ester of 1-piperidine Propionic Acid (021219)

The target molecule was synthesized as follows. A flask was charged with homocamptothecin (HCPT) (50 mg, 0.13 mmol) and then 15 mL of dry dichloromethane. The solution was allowed to stir for 10 minutes at ambient temperature. 1-(3-Dimethylamino-propyl)-3-ethyl-carbodiimide hydrochloride (EDCI) (147 mg, 0.79 mmol), 4-(dimethylamino) pyridine (DMAP) (17 mg, 0.17 mmol) and 1-piperdine propionic acid (69 mg, 0.43 mmol) were added. The reaction was allowed to stir for 20 hours at ambient temperature. The reaction was quenched and washed as described in the general procedure. The crude product was purified by flash chromatography (silica gel, 10:90 ethanol-ethyl acetate) to afford, after concentration of the appropriate fractions and removal of traces of solvent (vacuum pump), the title compound as a solid. $^1$H NMR (400 MHz, CDCl$_3$) δ 8.4 (s, 1H), 8.2 (d, 1H), 7.95 (d, 1H), 7.8 (t, 1H), 7.65 (t, 1H), 7.32 (s, 1H),5.60 (dd, 2H), 5.05 (s, 2H), 4.9 (s, 1H), 4.8(s, 1H), 3.2 (d, 1H), 3.1 (d, 1H), 2.9 (d, 1H), 2.8 (d, 1H), 2.6–2.4 (m, 4H), 2.1–1.8 (m, 6H), 1.6 (m, 2H), 1.2 (t, 3H).

B. By substituting other homo-camptothecin analogues for homo-camptothecin (hCPT) in part A of this example other compounds of this invention are prepared. In naming homo-camptothecin analogues, the standard numbering system for homo-camptothecin will be employed with "hCPT" being used as an abbreviation for homo-camptothecin. Other homo-camptothecin analogues include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy Hcpt (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;
9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 17

This Example provdes a method for making other compounds of this invention.

The general process is as follows:

An oven-dried round bottom flask containing a magnetic stirbar is allowed to cool to room temperature under vacuum and is then backfilled with nitrogen. The flask is charged with homocamptothecin (hCPT) (20 mg, 0.05 mmol) and then 5 mL of dry chloroform. The solution is allowed to stir for 10 minutes at ambient temperature. 1-(3-Dimethylamino-propyl)-3-ethyl-carbodiimide hydrochloride (EDCI) (44 mg, 0.23 mmol), 4-(dimethylamino) pyridine (DMAP) (5 mg, 0.036 mmol) and the appropriate acid (30 mg, 0.14 mmol) is added. The reaction is allowed to stir for 20 hours at ambient temperature. The reaction mixture is diluted with dichloromethane (25 mL) and washed with saturated aqueous sodium bicarbonate solution (3×15 mL). The organic layer is dried over anhydrous magnesium sulfate, filtered and concentrated under reduced pressure. The crude product is purified by flash chromatography (silica gel, 25:75 hexanes-ethyl acetate) to afford, after concentration of the appropriate fractions and removal of traces of solvent (vacuum pump), as a solid. Spectral data and a melting point are obtained.

A. Homocamptothecin-20-O ester of 1-BOC-piperidine-4-carboxylic Acid

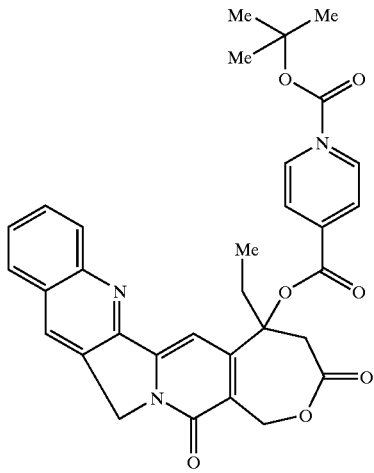

The target molecule is synthesized using the above procedure of this example. The flask is charged with homocamptothecin (hCPT) (20 mg, 0.05 mmol) and then 7 mL of dry chloroform. The solution will be allowed to stir for 10 minutes at ambient temperature. 1-(3-Dimethylamino-propyl)-3-ethyl-carbodiimide hydrochloride (EDCI) (61 mg, 0.31 mmol), 4-(dimethylamino)pyridine (DMAP) (12 mg, 0.12 mmol) and 1-BOC-piperdine-4-carboxylic acid (34 mg, 0.15 mmol) is added. The reaction will be allowed to stir for 20 hours at ambient temperature and worked up according to the procedure.

B. Homocamptothecin-20-O ester of N-morpholine Propionic Acid

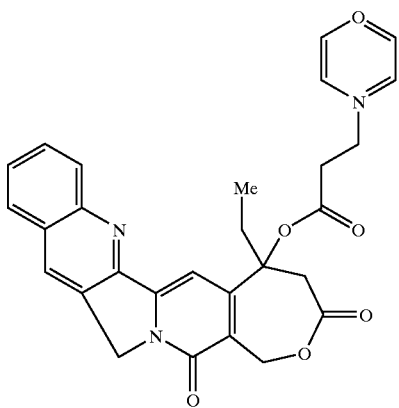

The target molecule is synthesized using the above procedure for this example. The flask is charged with homocamptothecin (hCPT) (20 mg, 0.05 mmol) and then 7 mL of dry chloroform. The solution is allowed to stir for 10 minutes at ambient temperature. 1-(3-Dimethylamino-propyl)-3-ethyl-carbodiimide hydrochloride (EDCI) (61 mg, 0.31 mmol), 4-(dimethylamino)pyridine (DMAP) (12 mg, 0.12 mmol) and N-morpholine propionic acid (23 mg, 0.15 mmol) is added. The reaction is allowed to stir for 20 hours at ambient temperature and worked up according to the procedure.

C. Homocamptothecin-20-O ester of 4-cyano-4-phenyl-piperidine Propionic Acid

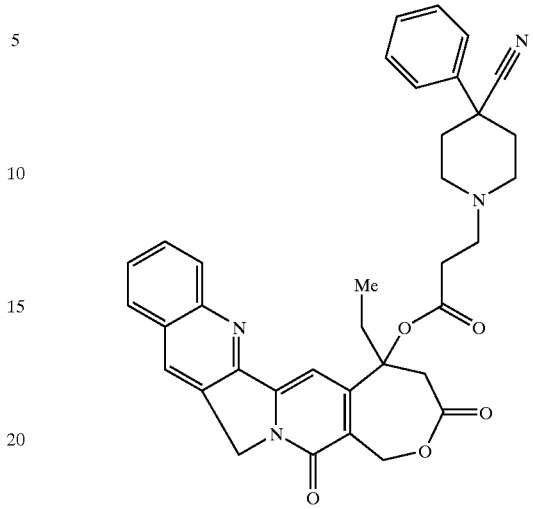

The target molecule is synthesized using the above procedure for this example. The flask is be charged with homocamptothecin (hCPT) (20 mg, 0.05 mmol) and then 7 mL of dry chloroform. The solution is allowed to stir for 10 minutes at ambient temperature. 1-(3-Dimethylamino-propyl)-3-ethyl-carbodiimide hydrochloride (EDCI) (61 mg, 0.31 mmol), 4-(dimethylamino)pyridine (DMAP) (12 mg, 0.12 mmol) and 4-cyano-4-phenyl-piperidine propionic acid (43 mg, 0.15 mmol) is added. The reaction is allowed to stir for 20 hours at ambient temperature and worked up according to the procedure.

D.
By substituting other homo-camptothecin analogues for homo-camptothecin (hCPT) in parts A-C of this example other compounds of this invention are. prepared. In naming homo-camptothecin analogues, the standard numbering system for homo-camptothecin will be employed with "hCPT" being used as an abbreviation for homo-camptothecin. Other homo-camptothecin analogues include the following:

10,11-methylenedioxy hCPT;
9-nitro hCPT;
9-amino hCPT;
9-amino-10-hydroxy hCPT;
9-methylamino hCPT;
9-dimethylamino hCPT;
9-dimethylaminomethyl-10-hydroxy Hcpt (homo topotecan);
9-piperidino hCPT;
9-morpholino hCPT
7-ethyl-10-[4-(1-piperidino)-1-piperidino]carbonyloxy)-hCPT (homo irinotecan);
7-t-butyldimethylsilyl hCPT;
7-t-butyldimethylsilyl-10-hydroxy hCPT;
9-nitro-10,11-methylenedioxy hCPT;
9-amino-10,11-methylenedioxy hCPT;
9-methyl-10,11-methylenedioxy hCPT;
9-chloro-10,11-methylenedioxy hCPT;
9-cyano-10,11-methylenedioxy hCPT;
9-acetyloxy-10,11-methylenedioxy hCPT;
9-acetylamino-10,11-methylenedioxy hCPT;
9-aminomethyl-10-hydroxy hCPT;

9-methylaminomethyl-10-hydroxy hCPT;
9-dimethylaminomethyl-10-hydroxy hCPT;
9-(2-hydroxyethyl)aminomethyl-10-hydroxy hCPT;
9-morpholinomethyl-10-hydroxy hCPT;
7-ethyl-10-hydroxy hCPT;
7-ethyl-10-acetyloxy hCPT;
7-methyl-10-aminocarbonyloxy hCPT;
7-n-propyl-10-piperidinocarbonyloxy hCPT;
7-ethyl-10-(2-dimethylamino)ethyl hCPT; and the like.

Example 18

This example provides directions for growing cells and testing compounds of the invention for their effect on the growth of the cells. All cells can be purchased from DCTDC Tumor Repository, NCI, NIH.

Cell Colony Formation Assay

Five hundred cells (VM46) are plated in 60 mm Petri dishes containing 2.7 ml of medium (modified McCoy's 5a medium containing 10% fetal bovine serum and 100 units/ml penicillin and 100 mg/ml streptomycin). The cells are incubated in a $CO_2$ incubator at 37° C. for 5 hours for attachment to the bottom of Petri dishes. Drugs are made fresh in medium at ten times the final concentration, and then 0.3 ml of this stock solution is added to the 2.7 ml of medium in the dish. The cells are then incubated with drugs for 72 hours at 37° C. At the end of the incubation the drug-containing media are decanted, the dishes are rinsed with 4 ml of Hank's Balance Salt Solution (HBSS), 5 ml of fresh medium is added, and the dishes are returned to the incubator for colony formation. The cell colonies are counted using colony counter after incubation for 8 days for VM46 cells. Cell survival (%) is calculated.

Values of ID50 (the drug concentration producing 50% inhibition of colony formation) may be determined for each tested compound. Results are shown in Table I for hCPT as a compound of this invention taught in Example 16.

TABLE I

| Compound | Value of ID50 (NM) |
|---|---|
| hCPT | 4 |
| 021219 | 3.5 |

Example 19

This Example Provides Directions for Performing In Vivo Toxicity Tests of the Compounds of the Invention on C3H/HeJ Mice.

Acute toxicities of the compounds of this invention are evaluated on C3H/HeJ mice (body weight 18–22 g). The MTD40 (maximum tolerated dose at day 40) values are determined by the standard procedure described by Gad and Chengelis (see, for example, "*Acute Toxicology Testing*," $2^{nd}$ Ed., Shayne O. Gad and Christopher P. Chengelis, pp. 186–195 (Academic Press).) In the consecutive type studies, 2 mice are dosed at low and moderate doses of 40 and 100 mg/kg. If no severe and irreversible toxicity (euthanasia is required) occurs at these doses, a new pair of animals is initiated at 180 mg/kg, which is 1.8 times higher than 100 mg/kg. Sequential dosages (about 3 doses on 3 pairs of animals, i.e., 2 mice for each drug dose) are increased by a factor of 1.8 until severe and irreversible toxicity (euthanasia is required) occurred. Then another pair of animals is initiated at the highest nonlethal dosage, and successive dosages were increased by a factor of 1.15. The result of this exercise is two dosages, one apparently nonlethal and the other lethal if severe and irreversible toxicity occurs and euthanasia is required, separated by a factor of 1.15. Six mice are dosed at each dosage. If no severe and irreversible toxicity occurs at the lower dosage and at least one with severe and irreversible toxicity occurs at the higher dose, then the lower dose is considered to be the MTD. The compounds of this invention are administered to C3H/HeJ mice by intraperitoneal injection. Drug toxicity is evaluated on mice checked daily for 45 days. The toxicity parameters reported will be the MTD40. The MTD is defined as the highest dose causing no severe irreversible toxicity in one treatment group, but at least one animal exhibiting severe and irreversible toxicity and being euthanized at the next higher dose.

Example 20

This example provides directions for performing in vivo efficacy tests of the compounds of the invention on C3H/HeJ mice bearing MTG-B tumors.

Studies on the compounds of this invention are performed on C3H/HeJ mice bearing MTG-B tumors. The tumors grow exponentially following implantation into the flanks of the mice and reached a diameter of 8 mm (268.08 $mm^3$) by day 7 to 10. Treatment is initiated at that time, with the first day of treatment designated as day 0 for calculation and plots. The mice are injected i.p. with three drug dose levels (⅓, ½, 1 5 MTD) using both a single injection and the schedule of Q2D 5 3 (every 2 days for a total of 3 treatments at ⅓ MTD). Control groups of mice bearing 8 mm diameter tumors are treated with vehicle alone. After drug treatment, the mice are observed twice a day. When a tumor reaches 1.5 g, the mouse bearing the tumor wis euthanized. Surviving days measured from day 0 for mice treated with anticancer drugs (T) and surviving days measured from day 0 for control mice (C) are recorded. Tumor growth inhibition values (T/C %) are calculated using the formula T/C %=(surviving days of mice treated with an anticancer drug T/surviving days of control mice C) 5 100%.

Tumor sizes may be measured by caliper every day. Daily measurement (mm) of solid tumor (length L and width W) in two dimensions is used to calculate the tumor weight [tumor weight=(length 5 $width^2$)/2] based on the interchangeable value of 1 $mm^3$=1 mg. Tumor growth delay (T–C value) is determined by calculation of the median time (in days) required for the treatment group and control group tumors to reach 1,000 mg. Tumor doubling time (Td) is measured, and tumor cell kill is calculated by the formula of log cell kill=(T–C value)/(3.32 5 Td). Regression effects after treatment may be observed and recorded (a complete regression: a regression below limit of palpation; a partial regression: a regression of more than 50% reduction in tumor mass).

Generally, the survival time of the control mice is six (6) days. A ratio of the extra days of survival of mice treated with the compounds of the invention (compared to control) to the extra days of survival of mice treated with taxol (compared to control), can be calculated. For example, if the mice survived 18 days as compared to 9 days for taxol-treated mice, the CD/Taxol ratio would be 18–6/9–6=12/3=4.

Example 21

This example provides guidance for determining the hydrolysis kinetics of the lactone ring (E) of homocamptothecin derivatives in the presence of different blood components. A quantitative $C_{18}$ reversed-phase high-performance liquid chromatography (HPLC) assay can be employed. A description is found at the following references:

J. Med. Chem. 2000, 43, 3970–3980;
Anal. Biochem. 1993, 212, 285–287; and
Biochemistry 1994, 33, 10325–10336.
See also J. Med. Chem. 1998, 41, 31–37.

Example 22

This example provides guidance for determining the inhibition of topoisomerase I. This procedure is an intact cell assay and is a modification of a published procedure found at Cancer Res. 1986, 46, 2021–2026. A more recent publication can be found at J. Med. Chem. 1993, 36 2689–2700 at 2699. Here the modification of the previous procedure was used to quantitate the amount of topoisomerase I mediated DNA cleavage in intact cells. The DNA of HL-60 cells growing in culture is labeled by [$^3$H] thymidine incorporation. The cells are exposed to compounds to be tested and lysed, and the protein is precipitated. Radioactive DNA in cleavable complex formation with topoisomerase I coprecipitates with the protein. The amount of cleavable complex formation is quantitated by counting the pellet with a liquid scintillation counter.

What is claimed is:

1. A compound of the formula

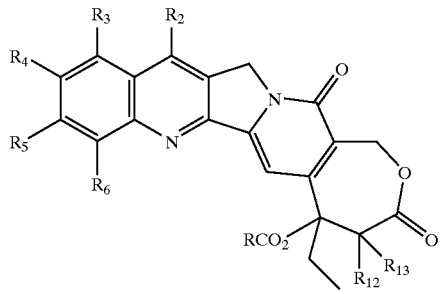

wherein R is $R_aR_bN$—$(CH_2)_m$; m is an integer from 1–10; and $R_2$ is hydrogen, halo, lower alkyl, lower alkoxy, hydroxy, RC(O)O (R is defined hereinbefore), cyano, nitro, amino, halogenated lower alkyl, halogenated lower alkoxy, hydroxycarbonyl, formyl, lower alkoxycarbonyl, tri lower alkylsilyl, lower alkylcarbonyloxy, lower alkylcarbonylamino, lower alkylcarbonyloxymethyl, substituted vinyl, 1-hydroxy-2-nitroethyl, alkoxycarbonylethyl, aminocarbonyl, alkylcarbonyl, alkylcarbonyloxymethyl, benzoylmethyl, benzylcarbonyloxymethyl, or mono- or di lower alkoxymethyl;

$R_3$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), $CH_2R_9$ (where $R_9$ is lower alkoxy, CN, amino lower alkoxy, mono- or di-lower alkylamino lower alkoxy, lower alkylthio, amino lower alkylthio, or mono- or di-lower alkylamino lower alkylthio), or $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), dialkylamino alkyl, lower alkylcarbonyloxy, or lower alkylcarbonylamino;

$R_4$ is hydrogen, halo, lower alkyl, lower alkoxy, hydroxy, RC(O)O (R is defined hereinbefore) cyano, nitro, amino, amino lower alkyl, halogenated lower alkyl, halogenated lower alkoxy, hydroxycarbonyl, formyl, lower alkoxycarbonyl, carbamoyloxy, lower alkylcarbonyloxy, or lower alkylcarbonylamino, or $R_4$ together with $R_5$ is methylenedioxy or ethylenedioxy;

$R_5$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino, or together with $R_4$ is methylenedioxy or ethylenedioxy;

$R_6$ is hydrogen, halo, lower alkyl, lower alkoxy, hydroxy, RC(O)O (R is defined hereinbefore) cyano, nitro, amino, halogenated lower alkyl, halogenated lower alkoxy, hydroxycarbonyl, formyl, lower alkoxycarbonyl, lower alkylcarbonyloxy, or lower alkylcarbonylamino; and $R_{12}$ and $R_{13}$ are independently hydrogen, lower alkyl, cyano, hydroxycarbonyl, lower alkoxycarbonyl, cycloalkyl, alkylcarbonylamino, 1-napthyl, 2-napthyl or phenyl.

2. The compound of claim 1, wherein each $R_2$ through $R_6$, $R_{12}$, and $R_{13}$ is H, m is 2, and $R_aR_bN$—$(CH_2)_m$ is a cyclic imide ring.

3. The compound of claim 1, wherein each of $R_2$ through $R_6$, $R_{12}$, and $R_{13}$ is H and $R_aR_bN$—$(CH_2)_m$ is 1-piperazinylethyl and the 1-piperazinyl ring is optionally substituted at the 4-position with an optionally substituted phenyl or benzyl.

4. The compound of claim 1, wherein m is 2; each of $R_2$ through $R_6$, $R_{12}$, and $R_{13}$ is H; and $R_aR_bN$—$(CH_2)_m$ is

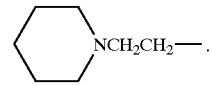

5. The compound of claim 1, wherein m is 2; each of $R_2$, $R_3$, $R_4$, $R_5$, $R_6$, $R_{12}$, and $R_{13}$ is hydrogen; and $R_aR_bN$ is cyclic amino or an imido ring.

6. The compound of claim 5, wherein $R_aR_bN$ is cyclic amino.

7. The compound of claim 5, wherein $R_aR_bN$ is an imido ring.

8. The compound of claim 1, wherein $R_2$ is hydrogen;

$R_3$ is $CH_2NR_7R_8$ (where each of $R_7$ and $R_8$ is independently H—, alkyl of 1–6 carbons, optionally substituted phenyl, hydroxy lower alkyl, amino lower alkyl, or mono- or dialkylamino lower alkyl, or $R_7$ and $R_8$ taken together with —N— represent a cyclic amino-), $NR_{10}R_{11}$ (where each of $R_{10}$ and $R_{11}$ is independently hydrogen, lower alkyl, phenyl, hydroxy lower alkyl, amino lower alkyl, or mono- or di-lower alkyl, or $R_{10}$ and $R_{11}$ taken together with —N— represent a cyclic amino), or dialkylamino alkyl;

$R_4$ is lower alkoxy, hydroxy, halogenated lower alkyl, halogenated lower alkoxy, hydroxycarbonyl, formyl, lower alkoxycarbonyl, carbamoyloxy, lower alkylcarbonyloxy, or $R_4$ together with $R_5$ is methylenedioxy or ethylenedioxy;

$R_5$ is hydrogen, or together with $R_4$ is methylenedioxy or ethylenedioxy;

$R_6$ is hydrogen.

9. The compound of claim 8, wherein $R_3$ is $CH_2NR_7R_8$ (where each of $R_7$ and $R_8$ is lower alkyl), $R_4$ is hydroxy, alkoxy or alkylcarbonyloxy and $R_{12}$ and $R_{13}$ are hydrogen.

10. The compound of claim 9, wherein $R_3$ is $CH_2N(CH_3)_2$ and $R_4$ is hydroxy.

11. The compound of claim 10 wherein m is 2 and $R_a$ and $R_b$ together with N form a 5- or 6-membered cyclic amino or cyclic imide ring.

12. The compound of claim 11 wherein $R_aR_b$ together with N form a saturated 6-membered cyclic amine optionally having one additional nitrogen in the ring.

13. The compound of claim 12, wherein the 6-membered cyclic amine is piperazine optionally substituted at the 4-position with phenyl, substituted phenyl, benzyl, or substituted benzyl.

14. The compound of claim 1, wherein $R_2$ is hydrogen, lower alkyl, or halogenated lower alkyl;

$R_3$ is hydrogen or lower alkyl;

$R_4$ is lower alkoxy, hydroxy, halogenated lower alkoxy, carbamoyloxy, lower alkylcarbonyloxy, or $R_4$ together with $R_5$ is methylenedioxy;

$R_5$ is hydrogen, or together with $R_4$ is methylenedioxy; and $R_6$ is hydrogen.

15. The compound of claim 14, wherein $R_3$ is hydrogen, $R_5$ is hydrogen, $R_4$ is carbamoyloxy and $R_{12}$ and $R_{13}$ are hydrogen.

16. The compound of claim 15, wherein $R_2$ is lower alkyl and $R_4$ is 4-(1-piperidino)-1-piperidinocarbonyloxy.

17. The compound of claim 16, wherein m is 2, $R_2$ is ethyl and $R_a$ and $R_b$ together with N form a cyclic imide ring.

18. The compound of claim 16 wherein m is 2 and $R_aR_b$ together with N form a saturated 5-, 6-, or 7-membered cyclic amine ring having no more than one additional nitrogen, oxygen, or sulfur atom in the ring, wherein the ring is unsubstituted or substituted with one or two substituents chosen from lower alkyl, lower cycloalkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkylamino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

19. The compound of claim 18, wherein $R_aR_b$ together with N form a saturated 6-membered cyclic amine optionally having one additional nitrogen in the ring.

20. The compound of claim 19, wherein the 6-membered cyclic amine is piperazine optionally substituted at the 4-position with phenyl, substituted phenyl, benzyl, or substituted benzyl.

21. The compound of claim 1, wherein $R_2$ is lower alkyl;

$R_3$ is hydrogen;

$R_4$ is hydroxy, lower alkoxy, halogenated lower alkoxy, hydroxycarbonyl, formyl, lower alkoxycarbonyl, carbamoyloxy, lower alkylcarbonyloxy;

$R_5$ is hydrogen; and $R_6$ is hydrogen.

22. The compound of claim 21, wherein $R_2$ is ethyl, $R_4$ is hydroxy and $R_{12}$ and $R_{13}$ are hydrogen.

23. The compound of claim 22, wherein m is 2 and $R_a$ and $R_b$ together with N form a 5- or 6-member cyclic imide ring.

24. The compound of claim 22, wherein m is 2 and $R_aR_b$ together with N form a saturated 5-, 6-, or 7-membered cyclic amine ring having no more than one additional nitrogen, oxygen, or sulfur atom in the ring, wherein the ring is unsubstituted or substituted with one or two substituents chosen from lower alkyl, lower cycloalkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkylamino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

25. The compound of claim 21, wherein $R_aR_b$ together with N form a saturated 6-membered cyclic amine optionally having one additional nitrogen in the ring.

26. The compound of claim 1, wherein each of $R_2$, $R_4$, $R_5$, and $R_6$ is hydrogen;

$R_3$ is amino or nitro; and $R_{12}$ and $R_{13}$ are independently hydrogen, lower alkyl, cyano, hydroxycarbonyl, lower alkoxycarbonyl, cycloalkyl, alkylcarbonylamino, 1-napthyl, 2-napthyl or phenyl.

27. The compound of claim 26, wherein $R_3$ is amino and $R_{12}$ and $R_{13}$ are hydrogen.

28. The compound of claim 27, wherein m is 2 and $R_a$ and $R_b$ together with N form a cyclic imide ring.

29. The compound of claim 27, wherein m is 2 and $R_aR_b$ together with N form a saturated 5-, 6-, or 7-membered cyclic amine ring having no more than one additional nitrogen, oxygen, or sulfur atom in the ring, wherein the ring is unsubstituted or substituted with one or two substituents chosen from lower alkyl, lower cycloalkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkylamino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

30. The compound of claim 29, wherein $R_aR_b$ together with N form a saturated 6-membered cyclic amine optionally having one additional nitrogen in the ring.

31. The compound of claim 29, wherein $R_3$ is nitro.

32. The compound of claim 31, wherein m is 2 and $R_a$ and $R_b$ together with N form a cyclic imide ring.

33. The compound of claim 31, wherein m is 2 and $R_aR_b$ together with N form a saturated 5-, 6-, or 7-membered cyclic amine ring having no more than one additional nitrogen, oxygen, or sulfur atom in the ring, wherein the ring is unsubstituted or substituted with one or two substituents chosen from lower alkyl, lower cycloalkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkylamino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

34. The compound of claim 33, wherein $R_aR_b$ together with N form a saturated 6-membered cyclic amine optionally having one additional nitrogen in the ring.

35. The compound of claim 1, wherein $R_2$ is tri-lower alkylsilyl;

$R_3$ is hydrogen;

$R_4$ is hydroxy, lower alkoxy, halogenated lower alkoxy, hydroxycarbonyl, formyl, lower alkoxycarbonyl, carbamoyloxy, lower alkylcarbonyloxy;

$R_5$ is hydrogen; and $R_6$ is hydrogen.

36. The compound of claim 35, wherein $R_2$ is t-butyldimethylsilyl, $R_4$ is hydroxy $R_{12}$ and $R_{13}$ are hydrogen.

37. The compound of claim 36, wherein m is 2 and $R_a$ and $R_b$ together with N form a cyclic imide ring.

38. The compound of claim 36, wherein m is 2 and $R_aR_b$ together with N form a saturated 5-, 6-, or 7-membered cyclic amine ring having no more than one additional nitrogen, oxygen, or sulfur atom in the ring, wherein the ring is unsubstituted or substituted with one or two substituents chosen from lower alkyl, lower cycloalkyl, phenyl, substituted phenyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), benzyl, substituted benzyl (substituted with one to five substituents independently selected from the group consisting of halo, lower alkyl, lower alkoxy, hydroxy, cyano, nitro, amino, halogenated lower alkyl, halogenated lower alkoxy, carbonyl, hydroxycarbonyl, lower alkylcarbonyloxy, benzyloxy, optionally substituted piperidino, lower alkoxycarbonyl, and lower alkylcarbonylamino), aminocarbonylmethyl, lower alkylaminocarbonylmethyl, amino, mono- or di-lower alkylamino, cyclic amino, or a 5- or 6-membered heterocyclic ring optionally substituted with one or two substituents selected from the group consisting of halo, lower alkyl, lower alkoxy, hydroxy, cyano, nitro, amino, halogenated lower alkyl, halogenated lower alkoxy, hydroxycarbonyl, lower alkoxycarbonyl, lower alkylcarbonyloxy, and lower alkylcarbonylamino.

39. The compound of claim 38, wherein $R_aR_b$ together with N form a saturated 6-membered cyclic amine optionally having one additional nitrogen in the ring.

40. A pharmaceutical composition useful for treating cancer in a warm-blooded animal, which composition comprises compound as defined in claim 1 in combination with a pharmaceutically acceptable excipient.

41. The pharmaceutical composition of claim 40 suitable for oral administration.

42. The pharmaceutical composition of claim 40 suitable for IV administration.

43. The pharmaceutical composition of claim 40 suitable for IM administration.

44. A method for treating cancer in a warm-blooded animal, which method comprises administering a therapeutically effective amount of a compound as defined in claim 1.

45. The method of claim 44, wherein the compound is administered orally.

46. The method of claim 44, wherein the compound is administered IV.

47. The method of claim 44, wherein the compound is administered parenterally.

48. A compound of the formula

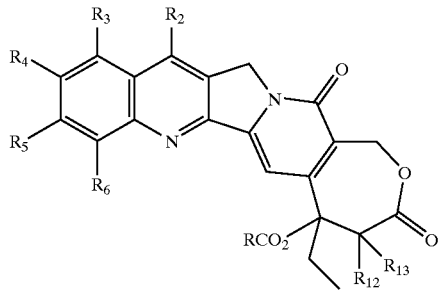

wherein R is $R_aR_bN-(CH_2)_m$; m is an integer from 1–10; and $R_2$ is $-CH_2NR_7R_8$ (where $R_7$ and $R_8$ taken together with $-N-$ represent a cyclic amino) when $R_3$ and $R_6$ are H and $R_4$ and $R_5$ taken together represent ethylenedioxy; or $R_2$ is butoxyiminomethyl when each of $R_3$, $R_4$, $R_5$ and $R_6$ is H; or $R_3$ is trialkylsilylethylene when each of $R_2$, $R_4$, $R_5$, and $R_6$ is H; or $R_2$ and $R_3$ together represent $-CH(NR_{12}R_{13})-CH_2-CH_2-$ when $R_4$ is lower alkyl, $R_5$ is halo, and $R_6$ is H, wherein $R_{12}$ and $R_{13}$ each is independently H or lower alyl.

49. A pharmaceutical composition useful for treating cancer in a warm-blooded animal, which composition comprises compound as defined in claim 48 in combination with a pharmaceutically acceptable excipient.

50. A method for treating cancer in a warm-blooded animal, which method comprises administering a therapeutically effective amount of a compound as defined in claim 48.

* * * * *

UNITED STATES PATENT AND TRADEMARK OFFICE
CERTIFICATE OF CORRECTION

PATENT NO. : 6,933,302 B2
DATED : August 23, 2005
INVENTOR(S) : Li-Xi Yang

It is certified that error appears in the above-identified patent and that said Letters Patent is hereby corrected as shown below:

Column 45,
Line 44, replace "and" by -- and $R_aR_b$ together with N form a cyclic amine or imide ring; and --.

Column 51,
Line 17, replace "and" by -- and $R_aR_b$ together with N form a cyclic amine or imide ring; and --.

Signed and Sealed this

First Day of November, 2005

JON W. DUDAS
*Director of the United States Patent and Trademark Office*